US012807687B2

(12) United States Patent
Seubert et al.

(10) Patent No.: US 12,807,687 B2
(45) **Date of Patent: *Nov. 24, 2026**

(54) TAU IMMUNOTHERAPY

(71) Applicant: Prothena Biosciences Limited, Dublin (IE)

(72) Inventors: Peter Seubert, San Francisco, CA (US); Philip James Dolan, III, Union City, CA (US); Yue Liu, Foster City, CA (US); Robin Barbour, Walnut Creek, CA (US)

(73) Assignee: Prothena Biosciences Limited, Dublin (IE)

( * ) Notice: Subject to any disclaimer, the term of this patent is extended or adjusted under 35 U.S.C. 154(b) by 651 days.

This patent is subject to a terminal disclaimer.

(21) Appl. No.: 18/305,109

(22) Filed: Apr. 21, 2023

(65) Prior Publication Data

US 2023/0340094 A1 Oct. 26, 2023

Related U.S. Application Data

(62) Division of application No. 16/667,647, filed on Oct. 29, 2019, now Pat. No. 11,643,457, which is a division of application No. 14/776,724, filed as application No. PCT/US2014/025044 on Mar. 12, 2014, now Pat. No. 10,501,531.

(60) Provisional application No. 61/800,382, filed on Mar. 15, 2013, provisional application No. 61/780,624, filed on Mar. 13, 2013.

(51) Int. Cl.

| | |
|---|---|
| ***C07K 16/18*** | (2006.01) |
| ***A61K 39/00*** | (2006.01) |
| ***A61K 47/68*** | (2017.01) |
| ***A61P 25/28*** | (2006.01) |
| ***G01N 33/68*** | (2006.01) |

(52) U.S. Cl.

CPC .......... *C07K 16/18* (2013.01); *A61K 39/0007* (2013.01); *A61K 47/6843* (2017.08); *A61P 25/28* (2018.01); *G01N 33/6896* (2013.01); *A61K 2039/505* (2013.01); *A61K 2039/55* (2013.01); *C07K 2317/24* (2013.01); *C07K 2317/34* (2013.01); *C07K 2317/55* (2013.01); *C07K 2317/92* (2013.01); *G01N 2333/47* (2013.01); *G01N 2800/2821* (2013.01)

(58) Field of Classification Search

None

See application file for complete search history.

(56) References Cited

U.S. PATENT DOCUMENTS

| | | | |
|---|---|---|---|
| 4,634,664 | A | 1/1987 | Oestberg |
| 4,634,666 | A | 1/1987 | Engleman et al. |
| 5,057,540 | A | 10/1991 | Kensil et al. |
| 5,208,036 | A | 5/1993 | Eppstein et al. |
| 5,225,539 | A | 7/1993 | Winter |
| 5,264,618 | A | 11/1993 | Felgner et al. |
| 5,279,833 | A | 1/1994 | Rose |
| 5,283,185 | A | 2/1994 | Epand et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,585,089 | A | 12/1996 | Queen et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,643,576 | A | 7/1997 | Johnston et al. |
| 5,661,016 | A | 8/1997 | Lonberg et al. |
| 5,733,743 | A | 3/1998 | Johnston et al. |
| 5,736,142 | A | 4/1998 | Sette et al. |
| 5,770,429 | A | 6/1998 | Johnston et al. |
| 5,786,464 | A | 7/1998 | Seed |
| 5,789,650 | A | 8/1998 | Lonberg et al. |
| 5,814,318 | A | 9/1998 | Lonberg et al. |
| 5,834,597 | A | 11/1998 | Tso et al. |
| 5,837,242 | A | 11/1998 | Holliger et al. |
| 5,858,657 | A | 1/1999 | Winter et al. |
| 5,859,205 | A | 1/1999 | Adair et al. |
| 5,871,907 | A | 2/1999 | Winter et al. |
| 5,874,299 | A | 2/1999 | Lonberg et al. |
| 5,877,218 | A | 3/1999 | Herzig et al. |
| 5,877,397 | A | 3/1999 | Lonberg et al. |
| 5,888,809 | A | 3/1999 | Allison |
| 6,063,598 | A | 5/2000 | Enenkel et al. |
| 6,114,148 | A | 9/2000 | Seed et al. |
| 6,407,213 | B1 | 6/2002 | Carter et al. |
| 6,624,821 | B1 | 9/2003 | Shin et al. |

(Continued)

FOREIGN PATENT DOCUMENTS

| | | |
|---|---|---|
| EP | 0673418 | 5/1998 |
| EP | 1355949 | 3/2010 |

(Continued)

OTHER PUBLICATIONS

Agadjanyan et al., "Humanized monoclonal antibody armanezumab specific to Nterminus of pathological tau: characterization and therapeutic potency," Molecular Neurodegeneration, 12:33, May 5, 2017, 18 pages.

(Continued)

*Primary Examiner* — Michael Szperka

(74) *Attorney, Agent, or Firm* — Fish & Richardson P.C.

(57) ABSTRACT

The invention provides antibodies to tau. The antibodies inhibit or delay tau-associated pathologies and associated symptomatic deterioration.

30 Claims, 7 Drawing Sheets

Specification includes a Sequence Listing.

(56) References Cited

U.S. PATENT DOCUMENTS

| | | | | |
|---|---|---|---|---|
| 6,881,557 | B2 | 4/2005 | Foote | |
| 7,442,516 | B2 | 10/2008 | Ohno et al. | |
| 7,569,339 | B2 | 8/2009 | Kaufmann et al. | |
| 8,012,936 | B2 | 9/2011 | Sigurdsson et al. | |
| 8,778,343 | B2 | 7/2014 | Kayed | |
| 8,926,974 | B2 | 1/2015 | Griswold-Prenner et al. | |
| 8,987,419 | B2 | 3/2015 | Barghorn et al. | |
| 9,051,367 | B2 | 6/2015 | Griswold-Prenner et al. | |
| 9,321,841 | B2 | 4/2016 | Jones et al. | |
| 9,605,054 | B2 | 3/2017 | Brady et al. | |
| 10,196,439 | B2 | 2/2019 | Pedersen et al. | |
| 10,253,100 | B2 | 4/2019 | Igawa et al. | |
| 10,301,379 | B2 | 5/2019 | Wadia et al. | |
| 10,478,142 | B2 | 11/2019 | Pedersen et al. | |
| 10,501,531 | B2 | 12/2019 | Seubert et al. | |
| 10,711,058 | B2 | 7/2020 | Adolfsson et al. | |
| 10,752,679 | B2 * | 8/2020 | Seubert | C07K 16/18 |
| 10,766,953 | B2 | 9/2020 | Mercken et al. | |
| 10,829,547 | B2 | 11/2020 | Roberts et al. | |
| 10,836,817 | B2 | 11/2020 | Adolfsson et al. | |
| 10,889,638 | B2 | 1/2021 | Barbour et al. | |
| 10,906,964 | B2 | 2/2021 | Barbour et al. | |
| 10,961,302 | B2 | 3/2021 | Barbour et al. | |
| 11,492,393 | B2 * | 11/2022 | Seubert | A61P 43/00 |
| 11,643,457 | B2 | 5/2023 | Seubert et al. | |
| 12,195,525 | B2 * | 1/2025 | Seubert | A61P 25/00 |
| 2004/0265920 | A1 | 12/2004 | Seubert et al. | |
| 2005/0114912 | A1 | 5/2005 | Botas et al. | |
| 2005/0132424 | A1 | 6/2005 | Lowe et al. | |
| 2007/0042359 | A1 | 2/2007 | Throsby et al. | |
| 2008/0050383 | A1 | 2/2008 | Sigurdsson et al. | |
| 2008/0076145 | A1 | 3/2008 | Cummings | |
| 2009/0028851 | A1 | 1/2009 | Stuhmer et al. | |
| 2010/0022026 | A1 | 1/2010 | Rump et al. | |
| 2010/0216703 | A1 | 8/2010 | Akassoglou | |
| 2010/0267927 | A1 | 10/2010 | Garrett et al. | |
| 2010/0316564 | A1 | 12/2010 | Sigurdsson | |
| 2011/0053264 | A1 | 3/2011 | Kashmiri et al. | |
| 2011/0206702 | A1 | 8/2011 | Polakis et al. | |
| 2012/0023911 | A1 | 2/2012 | Liu et al. | |
| 2012/0087861 | A1 * | 4/2012 | Nitsch | C07K 14/4711 424/9.34 |
| 2012/0100152 | A1 | 4/2012 | Roberts et al. | |
| 2012/0142602 | A1 | 6/2012 | Brady et al. | |
| 2012/0149880 | A1 | 6/2012 | Cheung et al. | |
| 2012/0204275 | A1 | 8/2012 | Schenk et al. | |
| 2012/0244174 | A1 * | 9/2012 | Chain | A61P 25/00 435/320.1 |
| 2012/0288507 | A1 | 11/2012 | Qian et al. | |
| 2012/0301473 | A1 * | 11/2012 | Binder | G01N 33/6896 424/139.1 |
| 2012/0308480 | A1 | 12/2012 | Smith et al. | |
| 2013/0189289 | A1 | 7/2013 | Inoue et al. | |
| 2013/0209453 | A1 | 8/2013 | Black et al. | |
| 2013/0295021 | A1 | 11/2013 | Chen et al. | |
| 2014/0056901 | A1 | 2/2014 | Agadjanyan et al. | |
| 2014/0086921 | A1 | 3/2014 | Griswold-Prenner et al. | |
| 2014/0171373 | A1 | 6/2014 | Ashe et al. | |
| 2014/0294731 | A1 | 10/2014 | Pfeifer et al. | |
| 2015/0050215 | A1 | 2/2015 | Novak et al. | |
| 2015/0050270 | A1 | 2/2015 | Sanofi | |
| 2015/0056721 | A1 | 2/2015 | Siman | |
| 2015/0166661 | A1 | 6/2015 | Chen et al. | |
| 2015/0175682 | A1 | 6/2015 | Pfeifer et al. | |
| 2015/0196663 | A1 | 7/2015 | Shusta et al. | |
| 2015/0253341 | A1 | 9/2015 | McAvoy et al. | |
| 2015/0266947 | A1 | 9/2015 | Sierks et al. | |
| 2016/0031976 | A1 | 2/2016 | Seubert et al. | |
| 2016/0289309 | A1 | 10/2016 | Griswold-Prenner et al. | |
| 2016/0376341 | A1 | 12/2016 | Adolfsson et al. | |
| 2017/0355756 | A1 | 12/2017 | Julien et al. | |
| 2018/0209994 | A1 | 7/2018 | Lannfelt et al. | |
| 2019/0322728 | A1 | 10/2019 | Seubert et al. | |
| 2019/0330314 | A1 | 10/2019 | Barbour et al. | |
| 2019/0330316 | A1 | 10/2019 | Barbour et al. | |
| 2020/0030445 | A1 | 1/2020 | John et al. | |
| 2020/0123239 | A1 | 4/2020 | Seubert et al. | |
| 2020/0131255 | A1 | 4/2020 | Kerchner et al. | |
| 2020/0181245 | A1 | 6/2020 | Masliah et al. | |
| 2021/0023216 | A1 | 1/2021 | Angstenberger et al. | |
| 2021/0032319 | A1 | 2/2021 | Seubert et al. | |
| 2021/0130449 | A1 | 5/2021 | Barbour et al. | |
| 2021/0261652 | A1 | 8/2021 | Nijjar et al. | |

FOREIGN PATENT DOCUMENTS

| | | |
|---|---|---|
| EP | 3080611 | 11/2018 |
| GB | 2220211 | 1/1996 |
| JP | 2009-056790 | 2/2009 |
| JP | 2010-511388 | 4/2010 |
| JP | 2011-501655 | 1/2011 |
| JP | 2012-500020 | 1/2012 |
| JP | 2014-530597 | 11/2014 |
| JP | 2015520685 | 7/2015 |
| JP | 2015-530971 | 10/2015 |
| JP | 2016-512551 | 4/2016 |
| WO | WO 1991/10741 | 7/1991 |
| WO | WO 1991/17271 | 11/1991 |
| WO | WO 1992/01047 | 1/1992 |
| WO | WO 1992/20791 | 11/1992 |
| WO | WO 1993/12227 | 6/1993 |
| WO | WO 1994/04678 | 3/1994 |
| WO | WO 1994/12629 | 6/1994 |
| WO | WO 1995/07707 | 3/1995 |
| WO | WO 1996/15452 | 5/1996 |
| WO | WO 1996/34625 | 11/1996 |
| WO | WO 1998/23635 | 6/1998 |
| WO | WO 1998/40100 | 9/1998 |
| WO | WO 2000/072880 | 12/2000 |
| WO | WO 2004/050884 | 7/2004 |
| WO | WO 2005/019442 | 10/2005 |
| WO | WO 2008/012142 | 1/2008 |
| WO | WO 2008/103472 | 8/2008 |
| WO | WO 2008/107388 | 9/2008 |
| WO | WO 2009/027471 | 3/2009 |
| WO | WO 2009/134711 | 11/2009 |
| WO | WO 2011/053565 | 5/2011 |
| WO | WO 2011/154321 | 12/2011 |
| WO | WO 2012/049570 | 4/2012 |
| WO | WO 2013/004717 | 1/2013 |
| WO | WO 2013/007839 | 1/2013 |
| WO | WO 2013/028810 | 2/2013 |
| WO | WO 2013/041962 | 3/2013 |
| WO | WO 2014/008404 | 1/2014 |
| WO | WO 2014/106000 | 6/2014 |
| WO | WO 2014/152157 | 9/2014 |
| WO | WO 2014/165271 | 10/2014 |
| WO | WO 2016/079597 | 5/2016 |
| WO | WO 2016/137950 | 9/2016 |
| WO | WO 2015/200806 | 12/2016 |
| WO | WO 2016/196726 | 12/2016 |
| WO | WO 2017/005732 | 1/2017 |
| WO | WO 2017/062672 | 4/2017 |
| WO | WO 2017/191559 | 11/2017 |
| WO | WO 2017/191560 | 11/2017 |
| WO | WO 2017/191561 | 11/2017 |
| WO | WO 2018/106781 | 6/2018 |
| WO | WO 2018/152359 | 8/2018 |
| WO | WO 2018/156250 | 8/2018 |
| WO | WO 2018/178077 | 10/2018 |
| WO | WO 2018/204546 | 11/2018 |
| WO | WO 2018/231254 | 12/2018 |
| WO | WO 2019/094595 | 5/2019 |
| WO | WO 2019/110571 | 6/2019 |
| WO | WO 2019/186276 | 10/2019 |
| WO | WO 2019/207159 | 10/2019 |
| WO | WO 2020/096608 | 5/2020 |
| WO | WO 2020/097561 | 5/2020 |
| WO | WO 2020/106598 | 5/2020 |
| WO | WO 2020/163817 | 8/2020 |
| WO | WO 2020/180819 | 9/2020 |

(56) References Cited

FOREIGN PATENT DOCUMENTS

WO WO 2020/193520 10/2020
WO WO 2021/010712 1/2021

OTHER PUBLICATIONS

Alexander et al., "Development of High Potency Universal DR-Restricted Helper Epitopes by Modification of High Affinity DR-Blocking Peptides, " Immunity, Dec. 1994, 1:751-761.
Almagro et al., "Humanization of antibodies", Frontiers in Bioscience, 13, 1619-1653, Jan. 1, 2008, 16 pages.
Amadoro et al., "A NH2 tau fragment targets neuronal mitochondria at AD synapses: possible implications for neurodegeneration" J. Alz. Dis., 2010, 21(2):445-470.
Andreadis et al., "Structure and novel exons of the human .tau. Gene," Biochemistry, 1992, 31:10626-1063.
Backsai et al., "Imaging of amyloid- deposits in brains of living mice permits direct observation of clearance of plaques with immunotherapy," Nature Medicine vol. 7, No. 3, Mar. 2001, pp. 369-372.
Bett et al., "Packaging Capacity and Stability of Human Adenovirus Type 5 Vectors," J. Virol., 1993, 67:5911-5921.
Boris-Lawrie et al., "Recent advances in retrovirus vector technology," Current Opinion in Genetics & Development, Feb. 1993, 3(1):102-109.
Castillo-Carranza et al., "Tau aggregates as immunotherapeutic targets," Frontiers in Bioscience, Scholar, Jan. 1, 2013, 5:426-438.
Chen et al., "Enhancement and destruction of antibody function by somatic mutation: unequal occurrence is controlled by V gene combinatorial associations," The EMBO Journal, 1995, 14(12):2784-2794.
Chicz et al., "Specificity and Promiscuity among Naturally Processed Peptides Bound to HLA-DR Alleles, " J. Exp. Med., 1993 178:27-47.
Chothia et al., "Canonical structures for the hypervariable regions of immunoglobulins," Journal of Molecular Biology, Aug. 1987, 196(4):901-917.
Chothia et al., "Conformations of immunoglobulin hypervariable regions," Nature, Dec. 1989, 342:878-883.
Co et al., "Chimeric and humanized antibodies with specificity for the CD33 antigen," J. Immunol., Feb. 1992, 148(4): 1149-1154.
Croft et al., "Novel monoclonal antibodies targeting the microtubule-binding domain of human tau," PLoS ONE, Apr. 2018, 13(4):e0195211.
Dubel "Molecular Engineering I: Humanization," Handbook of Therapeutic Antibodies, Chapter 6, pp. 119-144.
Dubensky et al., "Sindbis virus DNA-based expression vectors: utility for in vitro and in vivo gene transfer," J. Virol., Jan. 1996, 70(1):508-519.
EP 147783582 European Supplementary Search Report completed Nov. 3, 2016.
EP 18795047 Extended European Search Report mailed Feb. 2, 2021.
EP 19213368 Extended European Search Report mailed Jun. 24, 2020.
Falk et al., "Pool sequencing of natural HLA-DR, DQ, and DP ligands reveals detailed peptide motifs, constraints of processing, and general rules," Immunogenetics, 1994, 39:230-242.
Florenzano et al., "Extracellular truncated tau causes early presynaptic dysfunction associated with Alzheimer's disease and other tauopathies," Oncotarget, Apr. 2017, 8(29):64745-64778.
Foote et al., "Antibody framework residues affecting the conformation of the hypervariable loops," Journal of Molecular Biology, Mar. 1992, 224(2):487-499.
Gershoni et al., "Epitope Mapping, The First Step in Developing Epitope-Based Vaccines," Biodrugs, 2007, 21:(3), p. 145-156.
Ghoshal et al., "Tau Conformational Changes Correspond to Impairments of Episodic Memory in Mild Cognitive Impairment and Alzheimer's Disease, " Experimental Neurology, 2002, 177, 475-493 (Abstract Only).
Goedert et al., "Cloning and sequencing of the cDNA encoding a core protein of the paired helical filament of Alzheimer disease: Identification as the microtubule-associated protein tau," Proc. Natl. Acad. Sci. USA, 1998, 85:4051-4055.
Goedert et al., "Cloning and sequencing of the cDNA encoding an isoform of microtubule-associated protein tau containing four tandem repeats: differential expression of tau protein mRNAs in human brain," EMBO J., 1989, 8:393-399.
Goedert et al., "Multiple isoforms of human microtubule-associated protein tau: sequences and localization in neurofibrillary tangles of Alzheimer's disease," Neuron, Oct. 1989, 3:519-526.
Gonzales et al., "SDR grafting of a murine antibody using multiple human germline templates to minimize its immunogenicity," Mol. Immunol., Jul. 2004, 41(9):863-872.
Hammer et al., "Promiscuous and allele-specific anchors in HLA-DR-binding peptides, " Cell, Jul. 16, 1993, 74:197-203.
Hasegawa et al., "Characterization of Two distinct Monoclonal Antibodies to Paired Helical Filaments: Further Evidence for Fetal-Type Phosphorylation of the Tin Paired Helical Filaments", Journal of Neurochemistry, 1993, 60(6).
Hinton et al., "Engineered Human IgG Antibodies with Longer Serum Half-lives in Primates," J. Biol. Chem., Feb. 2004, 279(8):6213-6216.
Ittner et al., "Parkinsonism and impaired axonal transport in a mouse model of frontotemporal dementia," Proc. Natl. Acad. Sci. USA, Oct. 2008, 105(41):15997-16002.
Iwahashi et al., "CDR substitutions of a humanized monoclonal antibody (CC49): contributions of individual CDRs to antigen binding and immunogenicity," Mol. Immunol., 1999, 36(15-16):1079-1091.
Jack et al., "Hypothetical model of dynamic biomarkers of the Alzheimer's pathological cascade, " Lancet Neurol, Jan. 2010, 9:119-28.
Jicha et al., "Sequence Requirements for Formation of Conformational Variants of Tau Similar to Those Found in Alzheimer's Disease, " Journal of Neuroscience Research, Dec. 1999, 55:713-723.
Junghans et al., "Anti-Tac-H, a Humanized Antibody to the Interleukin 2 Receptor with New Features for Immunotherapy in Malignant and Immune Disorders, " Cancer Res., Mar. 1990, 50(5): 1495-1502.
Kawahara et al., "The Novel Monoclonal Antibody 9F5 Reveals Expression of a Fragment of GPNMB/Osteoactivin Processed by Furin-like Protease(s) in a Subpopulation of Microglia in Neonatal Rat Brain," GLIA, vol. 64, No. 11, pp. 1938-1961, (Nov. 2016).
Khlistunova et al., "Inhibition of Tau Aggregation in Cell Models of Tauopathy," Current Alzheimer Research, 2007, 4(5):544-546.
Kontsekova et al., "First-in-man tau vaccine targeting structural determinants essential for pathological tau-tau interaction reduces tau oligomerisation and neurofibrillary degeneration in an Alzheimer's disease model," *Alzheimer's Research & Therapy*, 6:44, (2014).
Kostelny et al., "Formation of a bispecific antibody by the use of leucine zippers," Journal of Immunology, Mar. 1992, 148(5):1547-1553.
Kussie et al., "A Single Engineered Amino Acid Substitution Changes Antibody Fine Specificity," J Immunol, 1994, 152(1):146-52.
Lander et al., "Mapping the Epitopes of Antibodies," Biotechnology and Genetic Engineering Reviews, 2007, 24:1-30.
Lantto et al., "Capturing the natural diversity of the human antibody response against vaccinia virus," J. Virol., Feb. 2011, 85:1820-1833.
Lazar et al., "A molecular immunology approach to antibody humanization and functional optimization", Molecular Immunology, 44:1986-1998 (2007).
Lazar et al., "Engineered antibody Fc variants with enhanced effector function," Proc. Natl. Acad. Sci. USA, Mar. 2006, 103(11):4005-4010.
Lee et al., "The microtubule binding domain of tau protein," Neuron, Jun. 1989, 2(6):1615-1624.
Leger et al., "Antibody Drug Discovery Chapter 1: Humanization of Antibodies", Molecular medicine and Medicinal Chemistry, Jan. 2011, pp. 1-23.
Lewis et al., "Neurofibrillary tangles, amyotrophy and progressive motor disturbance in mice expressing mutant (P301L) tau protein," Nature Genetics, 2000, 25:402-405.

(56) References Cited

OTHER PUBLICATIONS

Martin et al., "Structural Families in Loops of Homologous Proteins: Automatic Classification, Modelling and Application to Antibodies," Journal of Molecular Biology, Nov. 1996, 263(5):800-815.
McGee et al., "The encapsulation of a model protein in poly (D, L lactide-co-glycolide) microparticles of various sizes: an evaluation of process reproducibility," Journal of Microencapsulation, 1997, 14(2):197-210.
Morris "Epitope Mapping of Protein Antigens by Competition ELISA," The Protein Protocols Handbook, Walker ed., Jan. 1996, pp. 595-600.
Neuberger, "Generating high-avidity human Mabs in mice," Nature Biotechnology, 1996, 14:826.
Oddo et al., "Reduction of Soluble Aß and Tau, but Not Soluble Aß Alone, Ameliorates Cognitive Decline in Transgenic Mice with Plaques and Tangles," The Journal of Biological Chemistry, Dec. 22, 2016, 281(51):39413-39423.
Ohe et al., "Construction of a Novel Bovine Papillomavirus Vector Without Detectable Transforming Activity Suitable for Gene Transfer," Human Gene Therapy, 1995, 6(3):325-333.
Ostberg et al., "Human X (Mouse X Human) Hybridomas Stably Producing Human Antibodies," Hybridoma, 1983, 2(4):361-367.
Padlan, "A possible procedure for reducing the immunogenicity of antibody variable domains while preserving their ligand-binding properties," Mol. Immunol., 1991, 28(4-5):489-498.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol., Sep. 2002, 169(6):3076.
PCT /US2014/025044 International Preliminary Report on Patentability completed Oct. 9, 2014.
PCT/IB2017/052543 International Report on Patentability issued Nov. 6, 2018.
PCT/IB2017/052544 International Report on Patentability issued Nov. 6, 2018.
PCT/IB2017/052544 Search Report and Written Opinion mailed Jul. 19, 2017.
PCT/IB2017/052544 Search Report and Written Opinion mailed Jul. 31, 2017.
PCT/IB2017/052545 International Report on Patentability issued Nov. 6, 2018.
PCT/IB2017/052545 Search Report and Written Opinion mailed Aug. 1, 2017.
PCT/US2014/025044 International Search Report and Written Opinion mailed Nov. 3, 2014.
PCT/US2014/025044 Invitation to Pay Additional Fees and, Where Applicable, Protest Fee mailed Aug. 15, 2014.
PCT/US2018/030739 International Preliminary Report on Patentability mailed Nov. 5, 2019.
PCT/US2018/030739 International Search Report and Written Opinion mailed Nov. 5, 2018.
PCT/US2018/030739 International Search Report and Written Opinion mailed Sep. 18, 2018.
PCT/US2018/059895 International Preliminary Report on Patentability mailed May 11, 2021.
PCT/US2018/059895 International Search Report and Written Opinion mailed Apr. 12, 2019.
PCT/US2019/060616 International Search Report and Written Opinion mailed Mar. 20, 2020.
PCT/US2020/017357 International Preliminary Report on Patentability mailed Aug. 10, 2021.
PCT/US2020/017357 International Search Report and Written Opinion mailed Jun. 17, 2020.
PCT/US2020/017357 Invitation to Pay Additional Fees mailed Apr. 23, 2020.
PCT/US2020/020704 International Preliminary Report on Patentability mailed Aug. 25, 2021.
PCT/US2020/020704 Invitation to Pay Additional Fees mailed Jun. 3, 2020.
PCT/US2020/020704 Search Report and Written Opinion mailed Aug. 4, 2020.
Pedersen et al., "Tau immunotherapy for Alzheimer's disease," Trends in Molecular Medicine, Jun. 2015, 21(6):394-402.
Poorkaj et al., "Tau is a candidate gene for chromosome 17 frontotemporal dementia," Annals of Neurology, 1998, 43(6):815-825.
Powilleit et al., "Exploiting the Yeast L-A Viral Capsid for the In Vivo Assembly of Chimeric VLPs as Platform in Vaccine Development and Foreign Protein Expression," PLoS ONE, May 2007, 2(5):e415.
Queen et al., "Cell-Type Specific Regulation of a K Immunoglobulin Gene by Promoter and Enhancer Elements," Immunol. Rev., Feb. 1986, 89(1):49-68.
Rankin "Pseudo-phosphorylation of tau at Ser202 and Thr205 affects tau filament formation" Molecular Brain Research 138 (2005) 84-93 (Year: 2005).
Rosseels et al., "Tau Monoclonal Antibody Generation Based on Humanized Yeast Models," *Journal of Biological Chemistry,* vol. 290, No. 7, pp. 4059-4074, (Dec. 24, 2014).
Shirai et al., "H3-rules: identification of CDR-H3 structures in antibodies," FEES Lett., Jul. 15, 1999, 455:188-97.
Sinigaglia et al., "A malaria T-cell epitope recognized in association with most mouse and human MHC class II molecules," Nature, Dec. 1988, 336:778-780.
Songsivilai et al., "Bispecific antibody: a tool for diagnosis and treatment of disease," Clin. Exp. Immunol., Mar. 1990, 79(3):315-321.
Southwood et al., "Several Common HLA-DR Types Share Largely Overlapping Peptide Binding Repertoires," J. Immunology, Apr. 1998, 160(7):3363-3373.
Stoothoff "Tau phosphorylation: physiological and pathological consequences" Biochimica et Biophysica Acta 1739 (2005) 280-297 (Year: 2005).
Stoute et al., "A Preliminary Evaluation of a Recombinant Circumsporozoite Protein Vaccine against Plasmodium falciparum Malaria," The New England Journal of Medicine, Jan. 1997, 336(2):86-91.
Strang et al., "Generation and characterization of new monoclonal antibodies targeting the PHF1 and AT8 epitopes on human tau," Acta Neuropathologica Communications, 5:58, (2017).
Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, 164(3):1432-1441.
Vajdos et al., "Comprehensive Functional Maps of the Antigen-binding Site of an Anti-ErbB2 Antibody Obtained with Shotgun Scanning Mutagenesis," Journal of Molecular Biology, Jul. 2002, 320(2):415-428.
Vigo-Pelfrey et al., "Elevation of microtubule-associated protein tau in the cerebrospinal fluid of patients with Alzheimer's disease," Neurology, 1995, 45:788-793.
Ward et al., "Binding activities of a repertoire of single immunoglobulin variable domains secreted from *Escherichia coli,*" Nature, Oct. 1989, 341: 544-546.
Wu et al., "Simultaneous Humanization and Affinity Optimization of Monoclonal Antibodies", *Methods of Molecular Biology,* vol. 207: Recombinant Antibodies for Cancer Therapy: Methods and Protocols, Edited by M. Weischof and J. Krauss @ Humana Press Inc., Tolowa NJ, pp. 197-212 (Jan. 1, 2003).
Xiao et al., "High Efficiency, Long-Term Clinical Expression of Cottontail Rabbit Papillomavirus (CRPV) DNA in Rabbit Skin Following Particle-Mediated DNA Transfer," Nucleic Acids. Res., Jul. 1996, 24(13):2620-2622.
Yanamandra et al., "Anti-Tau Antibodies that Block Tau Aggregate Seeding In Vitro Markedly Decrease Pathology and Improve Cognition in Vivo," Neuron, Oct. 2013, 80:402-414.
Yanamandra et al., "Anti-tau antibody reduces insoluble tau and decreases brain atrophy," Annals of Clinical and Translational Neurology 2, 278-288 (2015).

(56) References Cited

OTHER PUBLICATIONS

Zhou et al., "Adeno-associated virus 2-mediated high efficiency gene transfer into immature and mature subsets of hematopoietic progenitor cells in human umbilical cord blood, " J. Exp. Med., Jun. 1994, 179(6):1867-1875.

* cited by examiner

TAU IMMUNOTHERAPY

CROSS-REFERENCE TO RELATED APPLICATIONS

This application is a divisional of U.S. application Ser. No. 16/667,647, filed Oct. 29, 2019, which is a divisional of U.S. application Ser. No. 14/776,724, now U.S. Pat. No. 10,501,531, filed Sep. 14, 2015, which is a National Stage Entry of PCT/US2014/025044 filed Mar. 12, 2014, which claims the benefit of U.S. Provisional Application Nos. 61/780,624 filed Mar. 13, 2013, and 61/800,382, filed Mar. 15, 2013, each incorporated by reference in its entirety for all purposes.

REFERENCE TO SEQUENCE LISTING

This application contains a Sequence Listing that has been submitted electronically as an XML file named 50887-0023003_SL_ST26.xml. The XML file, created on Apr. 20, 2023, is 38,953 bytes in size. The material in the XML file is hereby incorporated by reference in its entirety.

BACKGROUND

Tau is a well-known human protein that can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633(1992). Tau has been reported to have a role in stabilizing microtubules, particularly in the central nervous system. Total tau (t-tau, i.e., phosphorylated and unphosphorylated forms) and phospho-tau (p-tau, i.e., phosphorylated tau) are released by the brain in response to neuronal injury and neurodegeneration and have been reported to occur at increased levels in the CSF of Alzheimer's patients relative to the general population (Jack et al., Lancet Neurol 9:119-28 (2010)).

Tau is the principal constituent of neurofibrillary tangles, which together with plaques are a hallmark characteristic of Alzheimer's disease. The tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Hyperphosphorylated tau has also been reported to interfere with microtubule assembly, which may promote neuronal network breakdown.

Tau inclusions are part of the defining neurophathology of several neurodegenerative diseases including Alzheimer's disease, frontotemporal lobar degeneration, progressive supranuclear palsy and Pick's disease.

SUMMARY OF THE CLAIMED INVENTION

The invention provides monoclonal antibodies that compete for binding to tau with monoclonal antibody 16B5. Some antibodies are humanized, chimeric, veneered or human antibodies. Some antibodies are of human IgG isotype (e.g., IgG1, IgG2, or IgG4). Some such antibodies have a human IgG1 constant region having the sequence of SEQ ID NO: 29. Some antibodies have a human kappa constant region having the sequence of SEQ ID NO: 32. Some antibodies have at least one mutation in the constant region.

Some of the antibodies are a humanized, chimeric or veneered form of monoclonal antibody 16B5. Some antibodies have the three light chain CDRs as defined by Kabat and three heavy chain CDRs as defined by Kabat of monoclonal antibody 16B5. Some antibodies bind to tau in phosphorylated and unphosphorylated forms.

The invention further provides monoclonal antibodies that specifically bind to an epitope within residues 24-46 of SEQ ID NO:1 (Swiss-Prot No. P10636-8). Some such antibodies are human, humanized, chimeric, or veneered antibodies. Some antibodies specifically bind to an epitope within residues 25-44 of SEQ ID NO:1. Some antibodies specifically bind to an epitope within residues 30-39 of SEQ ID NO:1. Some antibodies bind to tau in phosphorylated and unphosphorylated forms.

The invention further provides monoclonal antibodies comprising a mature heavy chain variable region having an amino acid sequence at least 90% (e.g., at least 95%, at least 98%, at least 99%) identical to SEQ ID NO:15 and a mature light chain variable region at least 90% (e.g., at least 95%, at least 98%, at least 99%) identical to SEQ ID NO:22. In certain embodiments, the monoclonal antibody comprises three Kabat CDRs of SEQ ID NO:15 and three Kabat CDRs of SEQ ID NO:22. In some antibodies, the mature heavy chain variable region has an amino acid sequence designated SEQ ID NO:15 and the mature light chain variable region has an amino acid sequence designated SEQ ID NO:21, 22, or 23.

In some-antibodies, at least one of positions H13, H48 and H91 is occupied by K, M and F, respectively, and at least one of positions L1, L4, L36 and L43 is occupied by N, L, F and S, respectively. In some antibodies, positions H13, H48 and H91 are occupied by K, M and F, respectively, and at least two of positions L1, L4, L36 and L43 are occupied by N, L, F and S, respectively. In some antibodies, positions H13, H48 and H91 are occupied by K, M and F, respectively, and at least three of positions L1, L4, L36 and L43 are occupied by N, L, F and S, respectively. In some antibodies, positions H13, H48 and H91 are occupied by K, M and F, respectively, and positions L1, L4, L36 and L43 are occupied by N, L, F and S, respectively.

In some antibodies, the mature heavy chain variable region is fused to a heavy chain constant region and the mature light chain variable region is fused to a light chain constant region. In some antibodies, the heavy chain constant region is a mutant form of a natural human constant region which has reduced binding to an Fcγ receptor relative to the natural human constant region. In some antibodies, the heavy chain constant region is of IgG1 isotype.

In some antibodies, differences in the CDRs of the mature heavy chain variable region and mature light variable region from SEQ ID NOS: 15 and 22, respectively, reside in positions H60-H65.

The antibodies can be intact antibodies or fragments, such as a Fab fragment.

Any of the monoclonal antibodies or fragments can be conjugated to a cytotoxic or cytostatic agent.

The invention further provides methods of humanizing an antibody. Some methods comprise determining the sequences of the heavy and light chain variable regions of a mouse antibody; synthesizing a nucleic acid encoding a humanized heavy chain comprising CDRs of the mouse antibody heavy chain and a nucleic acid encoding a humanized light chain comprising CDRs of the mouse antibody light chain; and expressing the nucleic acids in a host cell to produce a humanized antibody, wherein the mouse antibody is 16B5.

The invention further provides methods of producing a humanized, chimeric or veneered antibody. Some methods comprise culturing cells transformed with nucleic acids encoding the heavy and light chains of the antibody, so that the cell secretes the antibody; and purifying the antibody from cell culture media, wherein the antibody is a humanized, chimeric or veneered form of 16B5.

The invention further provides methods of producing a cell line producing a humanized, chimeric or veneered antibody. Some methods comprise introducing a vector encoding heavy and light chains of an antibody and a selectable marker into cells; propagating the cells under conditions to select for cells having increased copy number of the vector; isolating single cells from the selected cells; and banking cells cloned from a single cell selected based on yield of antibody; wherein the antibody is a humanized, chimeric or veneered form of 16B5.

The invention further provides pharmaceutical compositions comprising any antibody disclosed herein and a pharmaceutically acceptable carrier.

The invention further provides nucleic acids comprising a segment encoding a heavy chain variable region having the sequence of SEQ ID NO: 10.

The invention further provides nucleic acids comprising a segment encoding a heavy chain variable region having the sequence of SEQ ID NO: 15. In some nucleic acids, the segment has a nucleotide sequence of SEQ ID NO: 25. Some nucleic acids further comprise a segment encoding an IgG1 constant region, optionally a human IgG1 constant region, for example, having a sequence of SEQ ID NO: 29 provided the C-terminal lysine can be omitted. In some nucleic acids, the segment encoding the IgG1 constant region has a nucleotide sequence of SEQ ID NO: 30. Some such nucleic acids further comprise an intron linking the segments encoding the heavy chain variable region and the IgG1 constant region. For example, the intron can have the sequence of the intron found in SEQ ID NO: 31. Thus, the intron and the segment encoding the IgG1 constant region can have a nucleotide sequence of SEQ ID NO: 31.

The invention further provides a nucleic acid comprising a segment encoding a light chain variable region having the sequence of SEQ ID NO: 16.

The invention further provides a nucleic acid comprising a segment encoding a light chain variable region having a sequence of SEQ ID NO: 21, 22, or 23. In some nucleic acids, the segment encoding the light chain variable region has the sequence of SEQ ID NO: 26, 27 or 28. Some such nucleic acids further comprise a segment encoding a kappa constant region. The kappa constant region can be a human kappa constant region and can have the sequence of SEQ ID NO: 32. Optionally, the nucleic acid encoding the kappa constant region has the sequence of SEQ ID NO: 33. Some such nucleic acids further comprise an intron linking the segment encoding the light chain variable region to the segment encoding the kappa constant region. For example, the intron can have the sequence of the intron found in SEQ ID NO: 34. Thus, the intron and the segment encoding the kappa constant region can have a nucleotide sequence of SEQ ID NO: 34.

Any of the above-mentioned antibodies can include a heavy chain comprising a human IgG1 constant region having the sequence of SEQ ID NO: 29 and/or a light chain comprising a human kappa constant region having the sequence of SEQ ID NO: 32.

The invention further provides an isolated fragment of tau including 3-10 contiguous residues of tau within residues 24-46 of SEQ ID NO:1 (Swiss-Prot No. P10636-8). Some fragments include 3-10 contiguous residues of tau within residues 30-39 of SEQ ID NO:1 (Swiss-Prot No. P10636-8). Some fragments include residues 33-37 of SEQ ID NO:1 (Swiss-Prot No. P10636-8). Some fragments are linked to a carrier molecule, optionally via a spacer that helps elicit antibodies against the fragment. Some fragments are part of a pharmaceutical composition comprising an adjuvant acceptable for administration to humans.

The invention further provides methods of treating or effecting prophylaxis of Alzheimer's disease. Some methods comprise administering an effective regime of an antibody that specifically binds to an epitope within residues 24-46 of SEQ ID NO:1 (Swiss-Prot No. P10636-8), or an agent that induces such an antibody, to a patient having or at risk of Alzheimer's disease and thereby treating or effecting prophylaxis of the disease. Preferably, the antibody is an antibody described herein. In some methods, the agent that induces the antibody is a fragment of tau that includes 3-10 contiguous residues of tau within residues 24-46 of SEQ ID NO: 1. In some methods, the patient is an ApoE4 carrier.

The invention further provides methods of treating or effecting prophylaxis of a disease associated with tau. Some methods comprise administering an effective regime of an antibody that specifically binds to an epitope within residues 24-46 of SEQ ID NO:1 (Swiss-Prot No. P10636-8), or an agent that induces such an antibody, to a patient having or at risk of the disease and thereby treating or effecting prophylaxis of the disease. Preferably, the antibody is an antibody described herein (e.g., a humanized 16B5 antibody). In some methods, the agent that induces the antibody is a fragment of tau that includes 3-10 contiguous residues of tau within residues 24-46 of SEQ ID NO:1. In some methods, the disease is a neurological disease.

The invention further provides methods of reducing aberrant transmission of tau. Some methods comprise administering an effective regime of an antibody that specifically binds to an epitope within residues 24-46 of SEQ ID NO:1 (Swiss-Prot No. P10636-8), or an agent that induces such an antibody, to a patient having or at risk of a disease associated with aberrant transmission of tau, and thereby treating or effecting prophylaxis of the disease. Preferably the antibody is an antibody described herein (e.g., a humanized 16B5 antibody). In some methods, the agent that induces the antibody is a fragment of tau that includes 3-10 contiguous residues of tau within residues 24-46 of SEQ ID NO: 1.

The invention further provides methods of inducing phagocytosis of tau. Some methods comprise administering an effective regime of an antibody that specifically binds to an epitope within residues 24-46 of SEQ ID NO:1 (Swiss-Prot No. P10636-8), or an agent that induces such an antibody, to a patient having or at risk of a disease associated with the accumulation of tau. Preferably, the antibody is an antibody described herein (e.g., a humanized 16B5 antibody). In some methods, the agent that induces the antibody is a fragment of tau that includes 3-10 contiguous residues of tau within residues 24-46 of SEQ ID NO: 1. In some methods, the disease is a neurological disease.

The invention further provides methods of inhibiting tau aggregation or deposition. In certain embodiments, the methods comprise administering an effective regime of an antibody that specifically binds to an epitope within residues 24-46 of SEQ ID NO:1 (Swiss-Prot No. P10636-8), or an agent that induces such an antibody, to a patient having or at risk of a disease associated with the aggregation or deposition of tau. Preferably, the antibody is an antibody described herein (e.g., a humanized 16B5 antibody). In some methods, the agent that induces the antibody is a fragment of tau that includes 3-10 contiguous residues of tau within residues 24-46 of SEQ ID NO: 1. In some methods, the disease is a neurological disease.

The invention further provides methods of inhibiting formation of tau tangles. Some methods comprise administering an effective regime of an antibody that specifically binds to an epitope within residues 24-46 of SEQ ID NO:1 (Swiss-Prot No. P10636-8), or an agent that induces such an antibody, to a patient having or at risk of a disease associated with the formation of tau tangles. Preferably, the antibody is an antibody described herein (e.g., a humanized 16B5 antibody). In some methods, the agent that induces the antibody is a fragment of tau that includes 3-10 contiguous residues of tau within residues 24-46 of SEQ ID NO: 1. In some methods, the disease is a neurological disease.

The invention further provides methods of screening an agent for activity against Alzheimer's disease. Some methods comprise administering the agent to a transgenic animal expressing a tau transgene, and determining whether the agent inhibits or delays at least one sign or symptom of Alzheimer's disease, wherein the agent is an antibody that specifically binds to an epitope within residues 24-46 of SEQ ID NO:1 (Swiss-Prot No. P10636-8), or an agent that induces such an antibody.

DEFINITIONS

Figure 1:
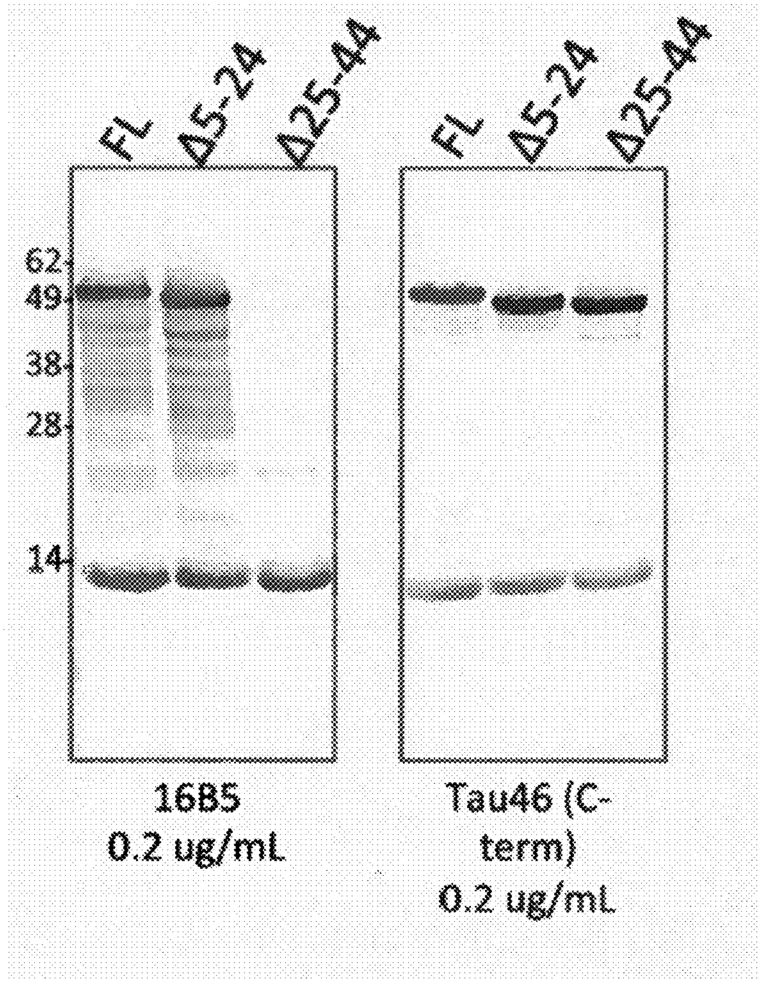
FIG. 1 depicts the results of experiments designed to map the epitope(s) bound by the 16B5 monoclonal antibody. Western blots containing full-length Tau or deletion mutants of Tau (Δ5-24 or Δ25-44) were stained with 16B5 antibodies (left panel) or Tau46 antibodies (right panel). The Tau46 antibody binds to the C-terminal epitope of Tau.

Monoclonal antibodies and other therapeutic agents are typically provided in isolated form. This means that the agent is typically at least 50% w/w pure of interfering proteins and other contaminants arising from its production or purification but does not exclude the possibility that the agent is combined with an excess of pharmaceutical acceptable carrier(s) or other vehicle intended to facilitate its use. Sometimes monoclonal antibodies (or other therapeutic agents) are at least 60%, 70%, 80%, 90%, 95% or 99% w/w pure of interfering proteins and contaminants from production or purification.

Antibodies of the invention typically bind to their designated target with an association constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function. A constant region can include any or all of a CH1 region, hinge region, CH2 region and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, MD, 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target. Fragments include separate heavy chains, light chains Fab, Fab', $F(ab')_2$, F(ab)c, Fv and single domain antibodies. Single (variable) domain antibodies include VH regions separated from their VL partners (or vice versa) in conventional antibodies (Ward et al., 1989, Nature 341:544-546) as well as VH regions (sometimes known as VHH) from species such as Camelidae or cartilaginous fish (e.g., a nurse shark) in which VH regions are not associated with VL regions (see, e.g., WO 9404678). Single domain antibodies in which one chain is separated from its natural partners are sometimes known as Dabs and single domain antibodies from Caemelidae or cartilaginous fish are sometimes known as nanobodies. Constant regions or parts of constant regions may or may not be present in single domain antibodies. For example, natural single variable region antibodies from Camelidae include a VHH variable region, and CH2 and CH3 constant regions. Single domain antibodies can be subject of humanization by analogous approaches to conventional antibodies. The Dabs type of antibodies are usually obtained from antibodies of human origin. NANOBODY types of antibody are of Camelidae or shark origin and can be subject to humanization. Fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. When an epitope is said to be within a range of amino acid residues in a protein (e.g., within residues 25 to 44 of tau), the range is inclusive of the residues defining its borders. Certain residues within the range contribute to the epitope, whereas others may not. The residues that form the epitope may or may not be contiguous with one another. Similarly, when an antibody binds to an epitope found within a particular range of amino acids, the antibody need not contact all the amino acids residues within the range, and the residues of the epitope that are contacted by the antibody may or may not be contiguous with one another. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other. The invention includes antibodies that compete with 16B5 and/or which bind to the same epitope on tau as 16B5.

Competition between antibodies is determined by an assay in which an antibody under test inhibits specific binding of a reference antibody (e.g. 16B5) to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages.

A disease is associated with tau if a population of patients with the disease have increased levels of tau in the brain, or increased deposition or inclusions of tau, or the presence of tau tangles in the brain, or increased phosphorylation of tau in the brain (average number of phosphate groups per molecule tau), or aberrant intercellular or intracellular transmission of tau compared with a population of subjects not known to have a neurological disease. A disease is also associated with tau if patients with a variant form of a tau gene have an increased risk of developing the disease relative to patients with a wildtype (most frequently occurring variant in a human population) tau gene.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

Statistical significance means $p \leq 0.05$.

DETAILED DESCRIPTION

I. General

The invention provides antibodies that bind to tau. Some antibodies specifically bind to an epitope within residues 23-46 of SEQ ID NO. 1. Some antibodies bind to tau irrespective of phosphorylation state. Some antibodies of the invention serve to inhibit or delay tau-associated pathologies and associated symptomatic deterioration. Although an understanding of mechanism is not required for practice of the invention, a reduction in toxicity may occur as a result of the antibody inducing phagocytosis of tau, inhibiting tau from inter or intramolecular aggregation, or from binding to other molecules, by stabilizing a non-toxic conformation, or by inhibiting intercellular or intracellular transmission of pathogenic tau forms, among other mechanisms. The antibodies of the invention or agents that induce such antibodies can be used in methods of treating or effecting prophylaxis of Alzheimer's and other diseases associated with tau.

II. Tau

Unless otherwise apparent from the context, reference to tau means a natural human form of tau including all isoforms irrespective of whether posttranslational modification (e.g., phosphorylation, glycation, or acetylation) is present. There are six major isoforms (splice variants) of tau occurring in the human brain. The longest of these variants has 441 amino acids, of which the initial met residue is cleaved. Residues are numbered according to the 441 isoform. Thus, for example, reference to a phosphorylation at position 404 means position 404 of the 441 isoform, or corresponding position of any other isoform when maximally aligned with the 441 isoform. The amino acid sequences of the isoforms and Swiss-Prot numbers are indicated below.

```
P10636-8
                                                        (SEQ ID NO: 1)
        10         20         30         40         50         60
MAEPRQEFEV MEDHAGTYGL GDRKDQGGYT MHQDQEGDTD AGLKESPLQT PTEDGSEEPG

        70         80         90        100        110        120
SETSDAKSTP TAEDVTAPLV DEGAPGKQAA AQPHTEIPEG TTAEEAGIGD TPSLEDEAAG

       130        140        150        160        170        180
HVTQARMVSK SKDGTGSDDK KAKGADGKTK IATPRGAAPP GQKGQANATR IPAKTPPAPK

       190        200        210        220        230        240
TPPSSGEPPK SGDRSGYSSP GSPGTPGSRS RTPSLPTPPT REPKKVAVVR TPPKSPSSAK

       250        260        270        280        290        300
SRLQTAPVPM PDLKNVKSKI GSTENLKHQP GGGKVQIINK KLDLSNVQSK CGSKDNIKHV

       310        320        330        340        350        360
PGGGSVQIVY KPVDLSKVTS KCGSLGNIHH KPGGGQVEVK SEKLDFKDRV QSKIGSLDNI

       370        380        390        400        410        420
THVPGGGNKK IETHKLTFRE NAKAKTDHGA EIVYKSPVVS GDTSPRHLSN VSSTGSIDMV

       430        440
DSPQLATLAD EVSASLAKQG L
```

-continued

P10636-7

(SEQ ID NO: 2)

10 20 30 40 50 60
MAEPRQEFEV MEDHAGTYGL GDRKDQGGYT MHQDQEGDTD AGLKESPLQT PTEDGSEEPG 70 80 90 100 110 120
SETSDAKSTP TAEAEEAGIG DTPSLEDEAA GHVTQARMVS KSKDGTGSDD KKAKGADGKT 130 140 150 160 170 180
KIATPRGAAP PGQKGQANAT RIPAKTPPAP KTPPSSGEPP KSGDRSGYSS PGSPGTPGSR 190 200 210 220 230 240
SRTPSLPTPP TREPKKVAVV RTPPKSPSSA KSRLQTAPVP MPDLKNVKSK IGSTENLKHQ 250 260 270 280 290 300
PGGGKVQIIN KKLDLSNVQS KCGSKDNIKH VPGGGSVQIV YKPVDLSKVT SKCGSLGNIH 310 320 330 340 350 360
HKPGGGQVEV KSEKLDFKDR VQSKIGSLDN ITHVPGGGNK KIETHKLTFR ENAKAKTDHG 370 380 390 400 410
AEIVYKSPVV SGDTSPRHLS NVSSTGSIDM VDSPQLATLA DEVSASLAKQ GL

P10636-6

(SEQ ID NO: 3)

10 20 30 40 50 60
MAEPRQEFEV MEDHAGTYGL GDRKDQGGYT MHQDQEGDTD AGLKAEEAGI GDTPSLEDEA 70 80 90 100 110 120
AGHVTQARMV SKSKDGTGSD DKKAKGADGK TKIATPRGAA PPGQKGQANA TRIPAKTPPA 130 140 150 160 170 180
PKTPPSSGEP PKSGDRSGYS SPGSPGTPGS RSRTPSLPTP PTREPKKVAV VRTPPKSPSS 190 200 210 220 230 240
AKSRLQTAPV PMPDLKNVKS KIGSTENLKH QPGGGKVQII NKKLDLSNVQ SKCGSKDNIK 250 260 270 280 290 300
HVPGGGSVQI VYKPVDLSKV TSKCGSLGNI HHKPGGGQVE VKSEKLDFKD RVQSKIGSLD 310 320 330 340 350 360
NITHVPGGGN KKIETHKLTF RENAKAKTDH GAEIVYKSPV VSGDTSPRHL SNVSSTGSID 370 380
MVDSPQLATL ADEVSASLAK QGL

P10636-5

(SEQ ID NO: 4)

10 20 30 40 50 60
MAEPRQEFEV MEDHAGTYGL GDRKDQGGYT MHQDQEGDTD AGLKESPLQT PTEDGSEEPG 70 80 90 100 110 120
SETSDAKSTP TAEDVTAPLV DEGAPGKQAA AQPHTEIPEG TTAEEAGIGD TPSLEDEAAG 130 140 150 160 170 180
HVTQARMVSK SKDGTGSDDK KAKGADGKTK IATPRGAAPP GQKGQANATR IPAKTPPAPK 190 200 210 220 230 240
TPPSSGEPPK SGDRSGYSSP GSPGTPGSRS RTPSLPTPPT REPKKVAVVR TPPKSPSSAK 250 260 270 280 290 300
SRLQTAPVPM PDLKNVKSKI GSTENLKHQP GGGKVQIVYK PVDLSKVTSK CGSLGNIHHK 310 320 330 340 350 360
PGGGQVEVKS EKLDFKDRVQ SKIGSLDNIT HVPGGGNKKI ETHKLTFREN AKAKTDHGAE 370 380 390 400 410
IVYKSPVVSG DTSPRHLSNV SSTGSIDMVD SPQLATLADE VSASLAKQGL

P10636-4

(SEQ ID NO: 5)

10 20 30 40 50 60
MAEPRQEFEV MEDHAGTYGL GDRKDQGGYT MHQDQEGDTD AGLKESPLQT PTEDGSEEPG 70 80 90 100 110 120
SETSDAKSTP TAEAEEAGIG DTPSLEDEAA GHVTQARMVS KSKDGTGSDD KKAKGADGKT 130 140 150 160 170 180
KIATPRGAAP PGQKGQANAT RIPAKTPPAP KTPPSSGEPP KSGDRSGYSS PGSPGTPGSR

-continued

```
       190        200        210        220        230        240
SRTPSLPTPP TREPKKVAVV RTPPKSPSSA KSRLQTAPVP MPDLKNVKSK IGSTENLKHQ

       250        260        270        280        290        300
PGGGKVQIVY KPVDLSKVTS KCGSLGNIHH KPGGGQVEVK SEKLDFKDRV QSKIGSLDNI

       310        320        330        340        350        360
THVPGGGNKK IETHKLTFRE NAKAKTDHGA EIVYKSPVVS GDTSPRHLSN VSSTGSIDMV

       370        380
DSPQLATLAD EVSASLAKQG L
```

P10636-2

```
                                                    (SEQ ID NO: 6)
        10         20         30         40         50         60
MAEPRQEFEV MEDHAGTYGL GDRKDQGGYT MHQDQEGDTD AGLKAEEAGI GDTPSLEDEA

        70         80         90        100        110        120
AGHVTQARMV SKSKDGTGSD DKKAKGADGK TKIATPRGAA PPGQKGQANA TRIPAKTPPA

       130        140        150        160        170        180
PKTPPSSGEP PKSGDRSGYS SPGSPGTPGS RSRTPSLPTP PTREPKKVAV VRTPPKSPSS

       190        200        210        220        230        240
AKSRLQTAPV PMPDLKNVKS KIGSTENLKH QPGGGKVQIV YKPVDLSKVT SKCGSLGNIH

       250        260        270        280        290        300
HKPGGGQVEV KSEKLDFKDR VQSKIGSLDN ITHVPGGGNK KIETHKLTFR ENAKAKTDHG

       310        320        330        340        350
AEIVYKSPVV SGDTSPRHLS NVSSTGSIDM VDSPQLATLA DEVSASLAKQ GL
```

Reference to tau includes known natural variations about 30 of which are listed in the Swiss-Pro database and permutations thereof, as well as mutations associated with tau pathologies, such as dementia, Pick's disease, supranuclear palsy, etc. (see, e.g., Swiss-Pro database and Poorkaj, et al. Ann Neurol. 43:815-825 (1998)). Some examples of tau mutations numbered by the 441 isoform are a lysine to threonine mutation at amino acid residue 257 (K257T), an isoleucine to valine mutation at amino acid position 260 (1260V); a glycine to valine mutation at amino acid position 272 (G272V); an asparagine to lysine mutation at amino acid position 279 (N279K); an asparagine to histidine mutation at amino acid position 296 (N296H); a proline to serine mutation at amino acid position 301 (P301S); a glycine to valine mutation at amino acid position 303 (G303V); a serine to asparagine mutation at position 305 (S305N); a glycine to serine mutation at amino acid position 335 (G335S); a valine to methionine mutation at position 337 (V337M); a glutamic acid to valine mutation at position 342 (E342V); a lysine to isoleucine mutation at amino acid position 369 (K3691); a glycine to arginine mutation at amino acid position 389 (G389R); and an arginine to tryptophan mutation at amino acid position 406 (R406W).

Tau can be phosphorylated at one or more amino acid residues including tyrosine at amino acid positions 18, 29, 97, 310, and 394 serine at amino acid positions 184, 185, 198, 199, 202, 208, 214, 235, 237, 238, 262, 293, 324, 356, 396, 400, 404, 409, 412, 413, and 422; and threonine at amino acids positions 175, 181, 205, 212, 217, 231, and 403.

III. Antibodies

A. Binding Specificity and Functional Properties

The invention provides antibodies that bind to tau. Some antibodies specifically bind to an epitope within residues 23-46 of SEQ ID NO:1. Some antibodies specifically bind to an epitope within residues 25-44 of SEQ ID NO:1. Some antibodies specifically bind to an epitope within 28-41 of SEQ ID NO:1. Some antibodies specifically bind to an epitope within residues 30-39 of SEQ ID NO:1. Some antibodies specifically bind to an epitope within residues 30-36 of SEQ ID NO:1. Some antibodies specifically bind to an epitope within residues 33-39 of SEQ ID NO: 1. Some antibodies specifically bind to an epitope within residues 33-36 of SEQ ID NO: 1. Some antibodies specifically bind to an epitope including residues 28-30, 28-31, 28-32, 28-33, 28-34, 28-35, 28-36, 28-37, 28-38, 28-39, 28-40, 28-41, 29-31, 29-32, 29-33, 29-34, 29-35, 29-36, 29-37, 29-38, 29-39, 29-40, 29-41, 30-32, 30-33, 30-34, 30-35, 30-36, 30-37, 30-38, 30-39, 30-40, 30-41, 31-33, 31-34, 31-35, 31-36, 31-37, 31-38, 31-39, 31-40, 31-41, 32-34, 32-35, 32-36, 32-37, 32-38, 32-39, 32-40, 32-41, 33-35, 33-36, 33-37, 33-38, 33-39, 33-40, 33-41, 34-36, 34-37, 34-38, 34-39, 34-40, 34-41, 35-37, 35-38, 35-39, 35-40, 35-41, 36-38, 36-39, 36-40, 36-41 of SEQ ID NO:1. Some antibodies bind to tau irrespective of phosphorylation state. Some antibodies bind to an epitope not including a residue subject to phosphorylation. These antibodies can be obtained by immunizing with a tau polypeptide purified from a natural source or recombinantly expressed. Antibodies can be screened for binding tau in unphosphorylated form as well as a form in which one or more residues susceptible to phosphorylation are phosphorylated. Such antibodies preferably bind with indistinguishable affinities or at least within a factor of 1.5, 2 or 3-fold to phosphorylated tau compared to non-phosphorylated tau (i.e., are "pan-specific). 16B5 is an example of a pan-specific monoclonal antibody. The invention also provides antibodies binding to the same epitope as any of the foregoing antibodies, such as, for example, the epitope of 16B5. Also included are antibodies competing for binding to tau with any of the foregoing antibodies, such as, for example, competing with 16B5.

The above-mentioned antibodies can be generated de novo by immunizing with a peptide including residues 23-46, 25-44, 28-30, 28-31, 28-32, 28-33, 28-34, 28-35, 28-36, 28-37, 28-38, 28-39, 28-40, 28-41, 29-31, 29-32, 29-33, 29-34, 29-35, 29-36, 29-37, 29-38, 29-39, 29-40, 29-41, 30-32, 30-33, 30-34, 30-35, 30-36, 30-37, 30-38, 30-39, 30-40, 30-41, 31-33, 31-34, 31-35, 31-36, 31-37, 31-38, 31-39, 31-40, 31-41, 32-34, 32-35, 32-36, 32-37, 32-38, 32-39, 32-40, 32-41, 33-35, 33-36, 33-37, 33-38, 33-39, 33-40, 33-41, 34-36, 34-37, 34-38, 34-39, 34-40, 34-41, 35-37, 35-38, 35-39, 35-40, 35-41, 36-38, 36-39, 36-40, 36-41 of SEQ ID NO:1 or by immunizing with a full length tau polypeptide or fragment thereof comprising such residues and screening for specific binding to a peptide including such residues. Such peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers are commonly used particularly keyhole limpet hemocyanin (KLH), ovalbumin and bovine serum albumin (BSA). Peptide spacers can be added to peptide immunogen as part of solid phase peptide synthesis. Carriers are typically added by chemical cross-linking. Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold. Spring Harbor Laboratory Press, Cold Spring Harbor, N.Y. 1988; Sinigaglia et al., Nature, 336:778-780 (1988); Chicz et al., J. Exp. Med., 178:27-47 (1993); Hammer et al., Cell 74:197-203 (1993); Falk K. et al., Immunogenetics, 39:230-242 (1994); WO 98/23635; and, Southwood et al. J. Immunology, 160: 3363-3373 (1998)). The carrier and spacer if present can be attached to either end of the immunogen.

A peptide with optional spacer and carrier can be used to immunize laboratory animals or B-cells as described in more detail below. Hybridoma supernatants can be tested for ability to bind one or more peptides including residues 24-46, 25-44, 28-30, 28-31, 28-32, 28-33, 28-34, 28-35, 28-36, 28-37, 28-38, 28-39, 28-40, 28-41, 29-31, 29-32, 29-33, 29-34, 29-35, 29-36, 29-37, 29-38, 29-39, 29-40, 29-41, 30-32, 30-33, 30-34, 30-35, 30-36, 30-37, 30-38, 30-39, 30-40, 30-41, 31-33, 31-34, 31-35, 31-36, 31-37, 31-38, 31-39, 31-40, 31-41, 32-34, 32-35, 32-36, 32-37, 32-38, 32-39, 32-40, 32-41, 33-35, 33-36, 33-37, 33-38, 33-39, 33-40, 33-41, 34-36, 34-37, 34-38, 34-39, 34-40, 34-41, 35-37, 35-38, 35-39, 35-40, 35-41, 36-38, 36-39, 36-40, 36-41 of SEQ ID NO:1 and/or phosphorylated and non-phosphorylated forms of tau, such as, for example, a full-length isoform of tau with position 404 in phosphorylated form. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the tau peptide. Any of the tau isoforms can be used.

Antibodies having the binding specificity of a selected murine antibody (e.g. 16B5) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for the desired target (e.g., a tau peptide) (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for the desired target are selected. The resulting antibodies usually have the same or similar epitope specificity as the murine starting material.

Other antibodies can be obtained by mutagenesis of cDNA encoding the heavy and light chains of an exemplary antibody, such as 16B5. Monoclonal antibodies that are at least 90%, 95% or 99% identical to 16B5 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one and preferably all six CDR(s) as defined by Kabat that are 90%, 95%, 99% or 100% identical to corresponding CDRs of 16B5 are also included.

B. Non-Human Antibodies

The production of other non-human monoclonal antibodies, e.g., murine, guinea pig, primate, rabbit or rat, against an immunogen can be performed by, for example, immunizing the animal with an immunogen as described above. See Harlow & Lane, *Antibodies, A Laboratory Manual* (CSHP NY, 1988) (incorporated by reference for all purposes). Such an immunogen can be obtained from a natural source, by peptide synthesis or by recombinant expression.

Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to Optionally, antibodies are further screened for binding to a specific region of tau. Such screening can be accomplished by determining binding of an antibody to a collection of deletion mutants of tau and determining which deletion mutants bind to the antibody. Binding can be assessed, for example, by Western blot, FACS™ or ELISA.

C. Humanized Antibodies

A humanized antibody is a genetically engineered antibody in which the CDRs from a non-human "donor" antibody (e.g., 16B5) are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881, 557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320:415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41:863, 2004. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 6 Å of a CDR region), (e.g., identified by modeling the light or heavy chain on the solved structure of a homologous known immunoglobulin chain); and (4) a residue participating in the VL-VH interface.

Framework residues from classes (1)-(3) as defined by Queen, U.S. Pat. No. 5,530,101 are sometimes alternately referred to as canonical and vernier residues. Framework residues defining canonical class of the donor CDR loops determining the conformation of a CDR loop are sometimes referred to as canonical residues (Chothia and Lesk, J. Mol. Biol. 196, 901-917 (1987), Thornton & Martin *J. Mol. Biol.,* 263, 800-815, 1996). A layer of framework residues that support antigen-binding loop conformations play a role in fine-tuning the fit of an antibody to antigen are sometimes referred to as vernier residues (Foote & Winter, 1992, *J Mol Bio.* 224, 487-499). Other candidates for substitution are residues creating a potential glycosylation site. Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position.

The invention provides humanized forms of the mouse 16B5 antibody. The mouse antibody comprises mature heavy and light chain variable regions having amino acid sequences comprising SEQ ID NOS. 10 and 16 respectively. The invention provides one exemplified humanized mature heavy chain variable regions (H1) and three exemplified humanized mature light chain variable region (L1, L2 and L3). The H1L2 variant has the same or better affinity as a chimeric 16B5 and seven backmutations. H1L1 and H1L3 have similar affinity to chimeric 16B5 and six backmutations The invention provides variants of the H1L2 humanized 16B5 antibody in which the humanized mature heavy chain variable region shows at least 90%, 95%, 96%, 97%, 98% or 99% identity to SEQ ID NO:15 and the humanized mature light chain mature variable region shows at least 90%, 95%, 96%, 97% 98% or 99% sequence identity to SEQ ID NO:22. Preferably, in such antibodies some or all of the backmutations in H1L2 are retained. In other words, at least 1, 2, or 3 of positions position H13 is occupied by K, position H48 is occupied by M and position H91 is occupied by F. Preferably at least, 1, 2, 3 or all four positions position L1 is occupied by N, position L4 is occupied by L, position L36 is occupied by F and position L43 is occupied by S. The CDR regions of such humanized antibodies are preferably identical or substantially identical to the CDR regions of H1L2, which are the same as those of the mouse donor antibody. The CDR regions can be defined by any conventional definition (e.g., Chothia) but are preferably as defined by Kabat.

One possibility for additional variation in 16B5 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutation. For example, when using a heavy chain acceptor sequence in which position H13 is already occupied by K no backmutation is necessary.

The invention also includes humanized antibodies in which the mature light and heavy chain variable regions shows at least 90, 95, 96, 97, 98 or 99% sequence identity to the mature light and heavy chain variable regions of the humanized 16B5 HIL1 antibody (SEQ ID NOs: 21 and 15, respectively) or the humanized 16B5 H1L3 antibody (SEQ ID NOs: 23 and 15, respectively).

D. Chimeric and Veneered Antibodies

The invention further provides chimeric and veneered forms of non-human antibodies, particularly 16B5 antibody.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of either the 16B5 antibody are included in the invention.

E. Human Antibodies

Human antibodies against tau are provided by a variety of techniques described below. Methods for producing human antibodies include the trioma method of Oestberg et al., *Hybridoma* 2:361-367 (1983); Oestberg, U.S. Pat. No. 4,634,664; and Engleman et al., US U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332.

F. Selection of Constant Region

The heavy and light chain variable regions of chimeric, humanized (including veneered), or human antibodies can be linked to at least a portion of a human constant region. The choice of constant region depends, in part, whether antibody-dependent complement and/or cellular mediated cytotoxicity is desired. For example, human isotopes IgG1 and IgG3 have complement-mediated cytotoxicity whereas human isotypes IgG2 and IgG4 have poor or no complement-mediated cytotoxicity. Light chain constant regions can be lambda or kappa. Antibodies can be expressed as tetramers containing two light and two heavy chains, as separate heavy chains, light chains, as Fab, Fab', $F(ab')_2$, and Fv, or as single chain antibodies in which heavy and light chain variable regions are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235 and 237 of human IgG1 is preferred for reducing effector functions. Optionally, positions 234, 236 and/or 237 in human IgG2 are substituted with alanine and position 235 with glutamine. (See, e.g., U.S. Pat. No. 5,624,821.)

G. Expression of Recombinant Antibodies

Chimeric, humanized (including veneered) and human antibodies are typically produced by recombinant expression. Nucleic acids encoding the antibodies can be codon-optimized for expression in the desired cell-type (e.g., CHO or Sp2/0). Nucleic acids encoding the humanized 16B5 heavy and light chain variable regions disclosed herein have sequences comprising or consisting of, for example, SEQ ID NO: 25 (encoding Hu16B5 H1), SEQ ID NO: 26 (encoding Hu16B5 L1), SEQ ID NO: 27 (encoding Hu16B5 L2), or SEQ ID NO: 28 (encoding Hu16B5 L3). For variable regions including signal peptides such as SEQ ID NOS. 10 and 16, the nucleic acid can encode the variable region with or without the signal peptide. Nucleic acid segments encoding heavy and light chain can be present on the same contiguous nucleic acid molecule or on separate molecules. The heavy and light chains can be expressed from the same vector or from different vectors. Nucleic acids are typically provided in isolated form.

Nucleic acids encoding a humanized 16B5 heavy chain variable region can be linked to a nucleic acid segment encoding a human IgG1 constant region, e.g., having the sequence of SEQ ID NO: 30. Such nucleic acids can also include an intron located between the segments encoding the heavy chain variable region and the IgG1 constant region, i.e., 5' to the segment encoding the constant region. An exemplary nucleic acid sequence encoding a human IgG1 constant region and having a mouse intron at its 5' end is shown in SEQ ID NO: 31.

Nucleic acids encoding humanized 16B5 light chain variable regions can be linked to a nucleic acid segment encoding a human kappa constant region, e.g., having the sequence of SEQ ID NO: 33. Such nucleic acids can also include an intron between the segments encoding the light chain variable region and the kappa constant region (i.e., 5' to the kappa constant region). An exemplary nucleic acid sequence encoding a human kappa constant region and having a human intron at its 5' end is shown in SEQ ID NO: 34.

Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase or glutamine synthase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Having introduced vector(s) encoding antibody heavy and light chains into cell culture, cell pools can be screened for growth productivity and product quality in serum-free media. Top-producing cell pools can then be subjected ot FACS-based single-cell cloning to generate monoclonal lines. Specific productivites above 50 μg or 100 μg per cell per day, which correspond to product titers of greater than 7.5 g/L culture, are preferred. Antibodies produced by single cell clones can also be tested for turbidity, filtration properties, PAGE, IEF, UV scan, HP-SEC, carboydrate-oligosaccharide mapping, mass spectrometery, and bining assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, Protein Purification (Springer-Verlag, NY, 1982)).

Methodology for commercial production of antibodies can be employed, including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

IV. Active Immunogens

An agent used for active immunization serves to induce in a patient the same types of antibody described in connection with passive immunization above. Agents used for active immunization can be the same types of immunogens used for generating monoclonal antibodies in laboratory animals, e.g., a peptide of 3-15 or 3-12 or 5-12, or 5-8 contiguous amino acids from a region of tau corresponding to residues 23-46, 25-44, 28-41 or 30-39 of SEQ ID NO. 1, such as, for example, a peptide including residues 28-30, 28-31, 28-32, 28-33, 28-34, 28-35, 28-36, 28-37, 28-38, 28-39, 28-40, 28-41, 29-31, 29-32, 29-33, 29-34, 29-35, 29-36, 29-37, 29-38, 29-39, 29-40, 29-41, 30-32, 30-33, 30-34, 30-35, 30-36, 30-37, 30-38, 30-39, 30-40, 30-41, 31-33, 31-34, 31-35, 31-36, 31-37, 31-38, 31-39, 31-40, 31-41, 32-34, 32-35, 32-36, 32-37, 32-38, 32-39, 32-40, 32-41, 33-35, 33-36, 33-37, 33-38, 33-39, 33-40, 33-41, 34-36, 34-37, 34-38, 34-39, 34-40, 34-41, 35-37, 35-38, 35-39, 35-40, 35-41, 36-38, 36-39, 36-40, 36-41 of SEQ ID NO:1. For inducing antibodies binding to the same or overlapping epitope as 16B5, the epitope specificity of these antibodies can be mapped (e.g., by testing binding to a series of overlapping peptides spanning tau). A fragment of tau consisting of or including or overlapping the epitope can then be used as an immunogen. Such fragments are typically used in unphosphorylated form.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam3Cys), mannan (a mannose polymer), or glucan (a β 1→2 polymer)), cytokines (e.g., IL-1, IL-1 alpha and β peptides, IL-2, γ-INF, IL-10, GM-CSF), and chemokines (e.g., MIP1-α and β, and RANTES). Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLOS ONE 2 (5): e415.) Alternatively, peptide immunogens can be linked to at least one artificial T-cell epitope capable of binding a large proportion of MHC Class II molecules, such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of tau to elicit an immune response. Preferred adjuvants augment the intrinsic response to an immunogen without causing conformational changes in the immunogen that affect the qualitative form of the response. Preferred adjuvants include aluminum salts, such aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). Stimulon™ QS-21 is a triterpene glycoside or saponin isolated from the bark of the Quillaja *Saponaria* Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, MA; now Antigenics, Inc., New York, NY). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of tau that induce antibodies against tau can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with tau peptides but nevertheless serve as mimetics of tau peptides and induce a similar immune response. Anti-idiotypic antibodies against monoclonal antibodies to tau as described above can also be used. Such anti-Id antibodies mimic the antigen and generate an immune response to it (see Essential Immunology, Roit ed., Blackwell Scientific Publications, Palo Alto, CA 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)); adenoviral vectors {see, e.g., Bett et al, J. Virol. 67, 591 1 (1993)); adeno-associated virus vectors {see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers and polylactides and poly(lactide-co-glycolides), (see, e.g., McGee et al., J. Micro Encap. 1996).

V. Screening Methods

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. The cells used for such screening are preferentially neuronal cells. A cellular model of tau pathology has been reported in which neuroblastoma cells are transfected with a four-repeat domain of tau, optionally with a mutation associated with tau pathology (e.g., delta K280, see Khlistunova, Current Alzheimer Research 4, 544-546 (2007)). In another model, tau is induced in the neuroblastoma N2a cell line by the addition of doxycyclinehe cell models enable one to study the toxicity of tau to cells in the soluble or aggregated state, the appearance of tau aggregates after switching on tau gene expression, the dissolution of tau aggregates after switching the gene expression off again, and the efficiency of antibodies in inhibiting formation of tau aggregates or disaggregating them.

Antibodies or active immunogens can also be screened in transgenic animal models of diseases associated with tau. Such transgenic animals can include a tau transgene (e.g., any of the human isoforms) and optionally a human APP transgene among others, such as a kinase that phosphorylates tau, ApoE, presenilin or alpha synuclein. Such transgenic animals are disposed to develop at least one sign or symptom of a disease associated with tau.

An exemplary transgenic animal is the K3 line of mice (Itner et al., Proc. Natl. Acad. Sci. USA 105(41):15997-6002 (2008)). These mice have a human tau transgene with a K 369 I mutation (the mutation is associated with Pick's disease) and a Thy 1.2 promoter. This model shows a rapid course of neurodegeneration, motor deficit and degeneration of afferent fibers and cerebellar granule cells. Another exemplary animal is the pR5 line of mice. These mice have a human tau transgene with a P301L mutation (the mutation is associated with frontotemporal dementia) and a Thy 1.2 promoter (Taconic, Germantown, N.Y., Lewis, et al., Nat Genet. 25:402-405 (2000)). These mice have a more gradual course of neurodegeneration. The mice develop neurofibrillary tangles in several brain regions and spinal cord, which is hereby incorporated by reference in its entirety). This is an excellent model to study the consequences of tangle development and for screening therapy that may inhibit the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored. Active immunization of these mice for 6-13 months with—AI wI KLH-PHF-1 generated titers of about 1,000 and showed fewer neurofibrillary tangles, less pSer422, and reduced weight loss relative to untreated control ice.

The activity of antibodies or active agents can be assessed by various criteria including reduction in amount of total tau or phosphorylated tau, reduction in other pathological characteristics, such as amyloid deposits of Aβ, and inhibition or delay or behavioral deficits. Active immunogens can also be tested for induction of antibodies in the sera. Both passive and active immunogens can be tested for passage of antibodies across the blood brain barrier into the brain of a transgenic animal. Antibodies or fragments inducing an antibody can also be tested in non-human primates that naturally or through induction develop symptoms of diseases characterized by tau. Tests on an antibody or active agent are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

VI. Patients Amenable to Treatment

The presence of neurofibrillary tangles has been found in several diseases including Alzheimer's disease, Down's syndrome, mild cognitive impairment, postencephalitic parkinsonism, posttraumatic dementia or dementia pugalistica, type C Niemann-Pick disease, supranuclear palsy, frontotemporal dementia, frontotemporal lobar degeneration, amyotrophic lateral sclerosis/parkinsonism dementia complex of Guam, and PSP progressive supranuclear palsy. The present regimes can also be used in treatment or prophylaxis of any of these diseases. Because of the widespread association between neurological diseases and conditions and tau, the present regimes can be used in treatment or prophylaxis of any subject showing elevated levels of tau or phosphorylated tau (e.g., in the CSF) compared with a mean value in individuals without neurological disease. The present regimes can also be used in treatment or prophylaxis of neurological disease in individuals having a mutation in tau associated with neurological disease. The present methods are particularly suitable for treatment or prophylaxis of Alzheimer's disease, and especially in patients.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in tau, such as those discussed above, as well as mutations in other genes associated with neurological disease. For example, the ApoE4 allele in heterozygous and even more so in homozygous form is associated with risk of Alzheimer's disease. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau or phospho-tau and Aβ42 levels. Elevated tau or phospho-tau and decreased Aβ42 levels signify the presence of AD. Some mutations associated with Parkinson's disease. Ala30Pro or Ala53, or mutations in other genes associated with Parkinson's disease such as leucine-rich repeat kinase, PARK8. Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

VII. Pharmaceutical Compositions and Methods of Treatment

In prophylactic applications, an antibody or agent for inducing an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay tau or phospho-tau and paired filaments formed from it in the brain, and/or inhibit or delay its toxic effects and/or inhibit/ or delay development of behavioral deficits. In therapeutic applications, an antibody or agent to induce an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of tau, phosphor-tau, or paired filaments formed from it, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

An exemplary dosage range for antibodies is from about 0.01 to 5 mg/kg, and more usually 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

The amount of an agent for active administration varies from 0.1-500 μg per patient and more usually from 1-100 or 1-10 μg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response.

Antibodies or agents for inducing antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against Aβ (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

VIII. In Vivo Imaging, Diagnostic Methods, and Optimizing Immunotherapy

The invention provides methods of in vivo imaging tau protein deposits (e.g., neurofibrillary tangles and tau inclusions) in a patient. The methods work by administering a reagent, such as antibody that binds tau (e.g., a mouse, humanized, chimeric or veneered16B5 antibody), to the patient and then detecting the agent after it has bound. Antibodies binding to an epitope of tau within amino acids 24 to 46 are preferred. In some methods, the antibody binds to an epitope within amino acids 25 to 44, or within amino acids 30 to 39. A clearing response to the administered antibodies can be avoided or reduced by using antibody fragments lacking a full-length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for tau is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

The methods of in vivo imaging of tau protein deposits are useful to diagnose or confirm diagnosis of a tauopathy, such as Alzheimer's disease, frontotemporal lobar degeneration, progressive supranuclear palsy and Pick's disease, or susceptibility to such a disease. For example, the methods can be used on a patient presenting with symptoms of dementia. If the patient has abnormal neurofibrillary tangles, then the patient is likely suffering from Alzheimer's disease. Alternatively, if the patient has abnormal tau inclusions, then depending on the location of the inclusions, the patient may be suffering from frontotemporal lobar degeneration. The methods can also be used on asymptomatic patients. Presence of abnormal tau protein deposits indicates susceptibility to future symptomatic disease. The methods are also useful for monitoring disease progression and/or response to treatment in patients who have been previously diagnosed with a tau-related disease.

Diagnosis can be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning tau immunotherapy treatment, and measured values thereafter compared with the baseline values. A decrease in values relative to baseline signals a positive response to treatment.

In some patients, diagnosis of a tauopathy may be aided by performing a PET scan. A PET scan can be performed using, for example, a conventional PET imager and auxiliary equipment. The scan typically includes one or more regions of the brain known in general to be associated with tau protein deposits and one or more regions in which few if any deposits are generally present to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, tau protein deposit detected. The results of the scan can also be presented numerically, with numbers relating to the amount of label detected and consequently amount of tau protein deposits. The label present in a region of the brain known to be associated with deposits for a particular tauopathy (e.g., Alzheimer's disease) can be compared with the label present in a region known not to be associated with deposits to provide a ratio indicative of the extent of deposits within the former region. For the same radiolabeled ligand, such ratios provide a comparable measure of tau protein deposits and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially tau deposits relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered16B5 antibody). The radioisotope used can be, for example, $C^{11}$, $N^{13}$, $O^{15}$, $F^{18}$, or $I^{23}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a tauopathy but are at elevated risk of developing a tauopathy. For asymptomatic patients, scans are particularly useful for individuals considered at elevated risk of tauopathy because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually. If a PET scan performed as a prophylactic measure indicates abnormally high levels of tau protein deposits, immunotherapy can be commenced and subsequent PET scans performed as in patients diagnosed with a tauopathy. If a PET scanned performed as a prophylactic measure indicates levels of tau protein deposits within normal levels, further PET scans can performed at intervals of between six months and 10 years, and preferably 1-5 years, as before, or in response to appearance of signs and symptoms of a tauopathy or mild cognitive impairment. By combining prophylactic scans with administration of tau-directed immunotherapy if and when an above normal level of tau protein deposits is detected, levels of tau protein deposits can be reduced to, or closer to, normal levels, or at least inhibited from increasing further, and the patient can remain free of the tauopathy for a longer period than if not receiving prophylactic scans and tau-directed immunotherapy (e.g., at least 5, 10, 15 or 20 years, or for the rest of the patient's life).

Normal levels of tau protein deposits can be determined by the amount of neurofibrillary tangles or tau inclusions in the brains of a representative sample of individuals in the general population who have not been diagnosed with a particular tauopathy (e.g., Alzheimer's disease) and are not considered at elevated risk of developing such disease (e.g., a representative sample of disease-free individuals under 50 years of age). Alternatively, a normal level can be recognized in an individual patient if the PET signal according to the present methods in a region of the brain in which tau protein deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau protein deposits compared with a region not known to be associated with deposits. For purposes of comparing the levels of tau protein deposits in an individual and population, the tau protein deposits should preferably be determined in the same region(s) of the brain, these regions including at least one region in which tau protein deposits associated with a particular tauopathy (e.g., Alzheimer's disease) are known to form. A patient having an elevated level of tau protein deposits is a candidate for commencing immunotherapy.

After commencing immunotherapy, a decrease in the level of tau protein deposits can be first seen as an indication that the treatment is having the desired effect. The observed decrease can be, for example, in the range of 1-100%, 1-50%, or 1-25% of the baseline value. Such effects can be measured in one or more regions of the brain in which deposits are known to form or can be measured from an average of such regions. The total effect of treatment can be approximated by adding the percentage reduction relative to baseline to the increase in tau protein deposits that would otherwise occur in an average untreated patient.

Maintenance of tau protein deposits at an approximately constant level or even a small increase in tau protein deposits can also be an indication of response to treatment albeit a suboptimal response. Such responses can be compared with a time course of levels of tau protein deposits in patients with a particular tauopathy (e.g., Alzheimer's disease) that did not receive treatment, to determine whether the immunotherapy is having an effect in inhibiting further increases of tau protein deposits.

Monitoring of changes in tau protein deposits allows adjustment of the immunotherapy or other treatment regime in response to the treatment. PET monitoring provides an indication of the nature and extent of response to treatment. Then a determination can be made whether to adjust treatment and if desired treatment can be adjusted in response to the PET monitoring. PET monitoring thus allows for tau-directed immunotherapy or other treatment regime to be adjusted before other biomarkers, MRI or cognitive measures have detectably responded. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing immunotherapy. A difference in response in à particular patient from the normal response in the control patient (e.g., mean plus variance of a standard deviation) can also provide evidence that an immunotherapy regime is or is not achieving a beneficial effect in a patient.

In some patients, monitoring indicates a detectable decline in tau protein deposits but that the level of tau protein deposits remains above normal. In such patients, if there are no unacceptable side effects, the treatment regime can be continued as is or even increased in frequency of administration and/or dose if not already at the maximum recommended dose.

If the monitoring indicates levels of tau protein deposits in a patient have already been reduced to normal, or near-normal, levels of tau protein deposits, the immunotherapy regime can be adjusted from one of induction (i.e., that reduces the level of tau protein deposits) to one of maintenance (i.e., that maintains tau protein deposits at an approximately constant level). Such . . . a regime can be affected by reducing the dose and or frequency of administering immunotherapy.

In other patients, monitoring can indicate that immunotherapy is having some beneficial effect but a suboptimal effect. An optimal effect can be defined as a percentage reduction in the level of tau protein deposits within the top half or quartile of the change in tau protein deposits (measured or calculated over the whole brain or representative region(s) thereof in which tau protein deposits are known to form) experienced by a representative sample of tauopathy patients undergoing immunotherapy at a given time point after commencing therapy. A patient experiencing a smaller decline or a patient whose tau protein deposits remains constant or even increases, but to a lesser extent than expected in the absence of immunotherapy (e.g., as inferred from a control group of patients not administered immunotherapy) can be classified as experiencing a positive but suboptimal response. Such patients can optionally be subject to an adjustment of regime in which the dose and or frequency of administration of an agent is increased.

In some patients, tau protein deposits may increase in similar or greater fashion to tau deposits in patients not receiving immunotherapy. If such increases persist over a period of time, such as 18 months or 2 years, even after any increase in the frequency or dose of agents, immunotherapy can if desired be discontinued in favor of other treatments.

The foregoing description of diagnosing, monitoring, and adjusting treatment for tauopathies has been largely focused on using PET scans. However, any other technique for visualizing and/or measuring tau protein deposits that is amenable to the use of tau antibodies of the invention (e.g., a mouse, humanized, chimeric or veneered16B5 antibody) can be used in place of PET scans to perform such methods.

EXAMPLES

Example 1. Generation of Antibody 16B5

Pan antibody 16B5, which recognizes tau whether or not it is phosphorylated, was raised to purified tau and selected based on its high affinity capture properties in an ELISA assay.

Example 2. Cloning and Sequencing of Antibody 16B5

RNA were extracted from pelleted cells expressing the 16B5 antibody using Trizol LS (Invitrogen). RNA concentrations were measured using the Quant-IT kit (Invitrogen).

5'-RACE was used to amplify the 5' end of IgG mRNA using the Smart RACE kit (Clontech). About 1 μg of RNA was used for the RT reaction and the cDNA pools were further amplified using the Universal primer provided with the Smart RACE kit and gene specific primers (GSPs) designed in ExonBIO.

Primer Sequences:

```
Universal Primer:
                                        (SEQ ID NO: 7)
CTAATACGACTCACTATAGGGC

GSPs:
IgG1 and IgG2a:
                                        (SEQ ID NO: 8)
CTC AAT TTT CTT GTC CAC CTT GGT GC

IgG2b:
                                        (SEQ ID NO: 9)
CTC AAG TTT TTT GTC CAC CGT GGT GC
```

PCR products were gel purified and cloned into the pSUPER-blunt vector (Adexon, www.adexonbiotech.com). For the heavy chain, 15 colonies were mini-prepared and sequenced. For the light chain, colony PCR was performed to distinguish endogenous aberrant light chain, and only clones that were not amplified from the colony PCR were sequenced. Sequencing results were analyzed on NTI vector. Adaptor and GSP primer sequences were marked on the map. The regions between the adaptor and GSP sequences are IgG heavy chain sequences which include leader, signal peptide and V-region, and part of the constant region. ORFs were marked on the map.

Example 3. Epitope Mapping of Antibody 16B5

Identification of epitope by peptide fragment analysis. The human tau sequence with 4 microtubule binding repeats and no N-terminal inserts, and containing a P301L mutation (rTau), was expressed in *E. coli* and purified. This form of tau has the sequence of SEQ ID NO:3, with the substitution of leucine for proline at position 243 (which corresponds to P301L using the numbering convention based on the longest isoform of tau). Enzymatic digests of 200 ug of tau were carried out with one of four different proteases: trypsin (which cleaves at the carboxyl end of arginine and lysine), chymotrypsin (which primarily cleaves at the carboxyl end of tyrosine, tryptophan, phenylalanine and leucine), LysC (which cleaves at the carboxyl end of lysine), or GluC (which cleaves after glutamate residues and rarely after aspartate residues). All proteases were obtained from Thermo Scientific, and digests were performed for 16 h at 37° C. The resulting peptide fragments were incubated with 10 μg of 16B5, and precipitated using Protein G magnetic beads (NEB). Precipitates were thoroughly washed in PBS containing 300 mM NaCl and 0.5% NP-40, then eluted with 1M NaCl in 100 mM glycine, pH 2.8. Eluates were dried under vacuum and resuspended in 0.1% trifluoroacetic acid (TFA). Resuspended eluates were loaded onto a 4.6×50 mm C18 column, then fractionated by HPLC (Agilent 1260 Infinity system) using a linear gradient of acetonitrile with 0.075% TFA. Peak fractions were collected, dried and resuspended in distilled water. Peptide masses and identities were determined by MALDI-TOF/TOF. A peak corresponding to residues 25-44 of SEQ ID NO:1 was identified in the LysC MS Spectrum. Peaks corresponding to residues 25-44 of SEQ ID NO:1 and 24-44 were identified in the Trypsin MS Spectrum. No signal was obtained from the chymotrypsin and GluC digests, suggesting that some epitopes may comprise residue 29 of SEQ ID NO:1 and/or residue 37 of SEQ ID NO:1.

Figure 2:
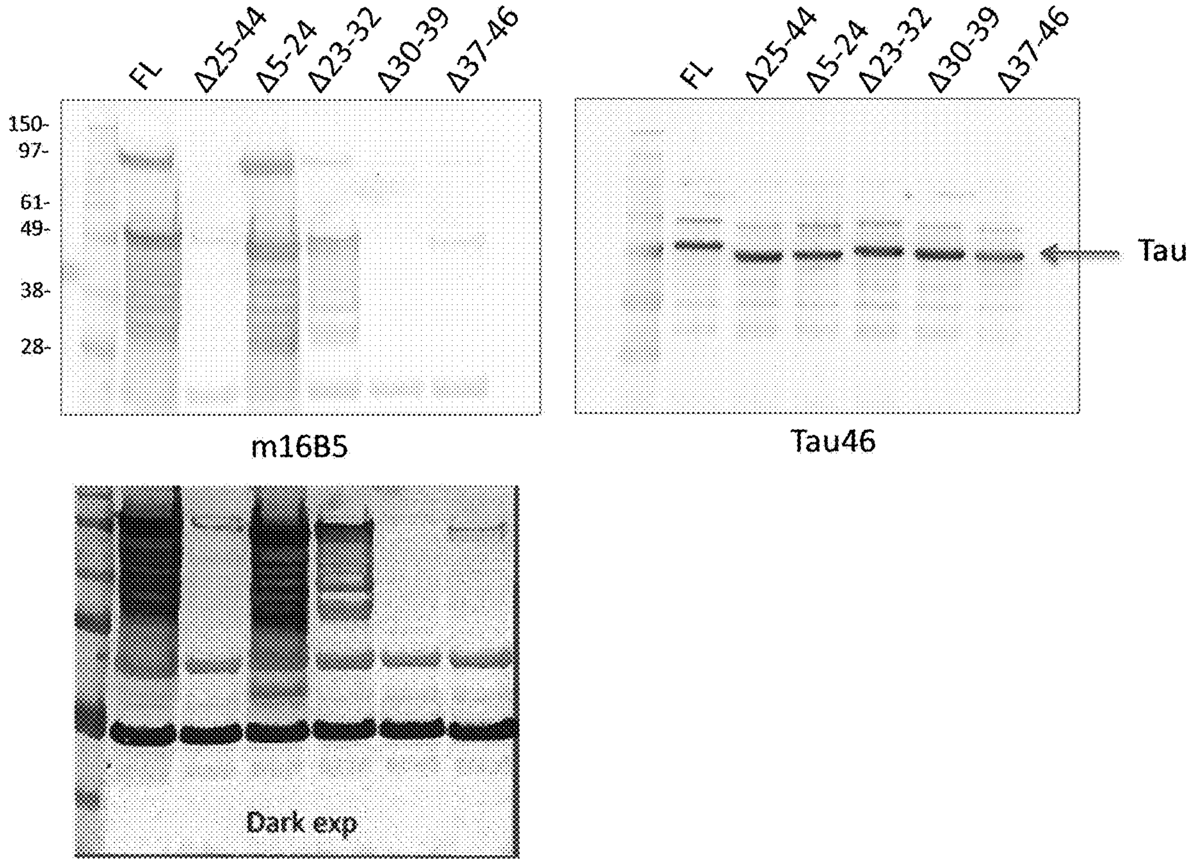
FIG. 2 depicts the results of experiments designed to map the epitope(s) bound by the 16B5 monoclonal antibody. Western blots containing full-length Tau or deletion mutants of Tau were stained with 16B5 antibodies (upper left panel) or Tau46 antibodies (right panel). A longer exposure of the blot stained with 16B5 antibodies is shown in the lower left panel. The deletion mutants of Tau analyzed in this experiment include Δ25-44, Δ5-24, Δ23-32, Δ30-39, and Δ37-46.

Identification of epitope by mutation analysis. Using the results determined by peptide fragment analysis (described above), deletion mutagenesis of rTau was carried out by whole plasmid amplification using standard molecular biology methods. Protein was expressed in small volumes of bacterial culture, and equal volumes of clarified bacterial lysate were electrophoresed, blotted, and stained with the 16B5 antibody. To control for sample loading, Tau46, an antibody with specificity for the C-terminal region of tau (C-terminal epitope), was used to stain duplicate blots. Both antibodies were used at a concentration of 0.2 μg/mL. Images were captured using a Licor Odyssey fluorescent scanner. The following deletion mutants of tau were made and analyzed in this manner: Δ5-24, Δ23-32, Δ25-44, Δ30-39, and Δ37-46. As shown in FIGS. 1 and 2, the Δ25-44 and Δ30-39 deletion mutants of tau were not detected by the 16B5 antibody, providing evidence that an epitope recognized by 16B5 lies within those residues. The Δ37-46 deletion mutant of tau was only slightly detectable with 16B5, providing evidence that some of the residues within 37-46 (e.g., residue 37) may play a role in the binding of 16B5 to tau. The 16B5 antibody stained the Δ23-32 deletion mutant of tau to a lesser extent than Δ5-24 and to a greater extent than the Δ25-44 and Δ30-39 deletion mutants, providing evidence that 16B5 may also bind to a peptide comprising residues 33-36, 30-36, 33-37, 30-37 or 33-39. Taken as a whole, the data obtained from the tau deletion mutants suggests that an epitope recognized by 16B5 may comprise some or all of residues 23-32 of SEQ ID NO: 1 and some or all of residues 37-46 of SEQ ID NO:1. For example, 16B5 may recognize an epitope within residues 32-38 or 28-41 of SEQ ID NO:1.

Figure 3:
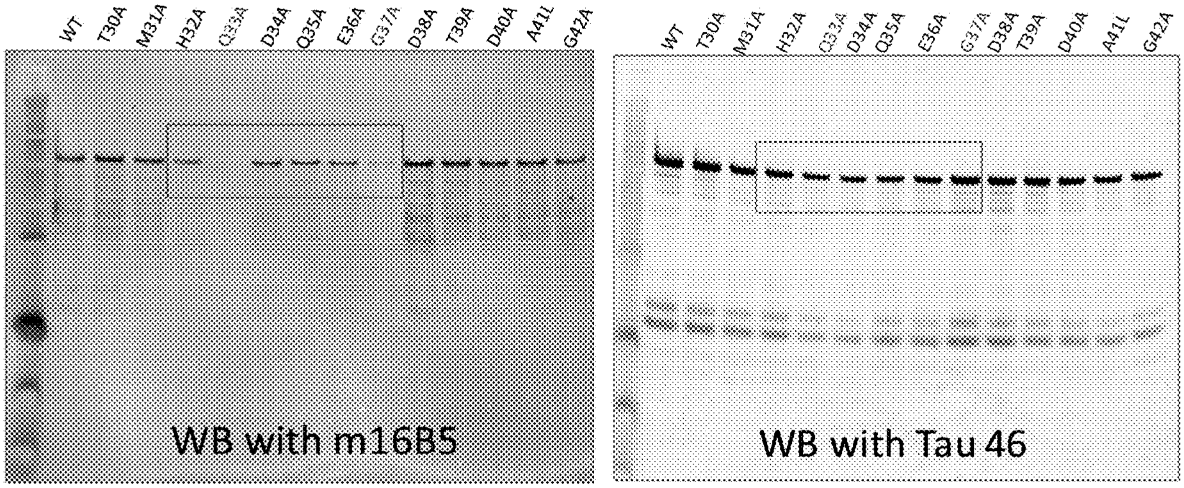
FIG. 3 depicts the results of an alanine scanning experiment designed to map the epitope(s) bound by the 16B5 monoclonal antibody. Western blots containing wild-type Tau (WT) or alanine point mutants of Tau were stained with 16B5 antibodies (left panel) or Tau46 antibodies (right panel). The alanine mutants of Tau analyzed in this experiment include T30A, M31A, H32A, Q33A, D34A, Q35A, E36A, G37A, D38A, T39A, D40A, A41L, and G42A.

Identification of epitope by alanine scanning. Single residues within the region of tau spanning residues 30-42 were next mutated to alanine using PCR mutagenesis. The mutated proteins were expressed, and lysates were resolved by electrophoresis and blotted with either the 16B5 antibody or the Tau46 antibody, as described above. The results of this analysis are shown in FIG. 3. The specific point mutants analyzed, including T30A, M31A, H32A, Q33A, D34A, Q35A, E36A, G37A, D38A, T39A, D40A, A41L, and G42A, are listed above the blots. Residues of particular interest are enclosed in boxes on each blot. Detectable binding of 16B5 was completely eliminated by the Q33A tau mutant and substantially reduced by the G37A tau mutant, providing evidence that residue 33, and to a lesser extent residue 37, may be important components of an epitope recognized by 16B5. Other residues may be important components of an epitope recognized by 16B5 in a Biacore analysis.

Example 4. Passive Immunization in the hTau.P301L Transgenic Mouse Model of Tauopathy Immunization. 3-month-old hTau.P301L-Tg female mice in the FVB/N genetic background were used for this study. Administration of 10 mg/kg of test and control antibodies was performed intraperitoneally, once a week. The treatment duration was about 5 months. Following 23 injections, the study ended with the sacrifice of the mice. Table 1 describes the test and control antibodies administered in this study.

TABLE 1

| Dosing Scheme | | |
|---|---|---|
| | Group K | Group M |
| Antibody | 16B5 | 6F10 |
| Binding specificity | Within 23-46 (see Example 3) | Non-immune IgG1 isotype control |
| N | 22 | 22 |
| Treatment | N2 | N3 |
| Dose | 10 mg/kg weekly | 10 mg/kg weekly |
| Dose volume | 1.724 ml/kg | 2.381 ml/kg |

Premature death is a phenotype observed in transgenic murine tauopathy models. The particular model used in this study develops hyperphosphorylated Tau at the age of 6 months, although with a high variability of onset. The mice also suffer motor defects like hind limb clasping and reduced general mobility, and die prematurely at the age of 8-11 months (reMYND unpublished data, Terwel et al., 2005). Mice developing end-stage disease symptoms, characterized by the presence of the clasping phenotype and weight loss, were sacrificed. An unexpectedly high number of mice died prematurely without the presence of these symptoms. The cause of death in such cases is considered to be unrelated to late-stage tauopathy or the test antibody, and instead is thought to be related to the inbred FVB/N background.

Table 2 shows an overview of the overall survival of all mice during the course of the study.

TABLE 2

| Survival during treatment (all causes of death) | | | | |
|---|---|---|---|---|
| | | N at study start | N alive at sacrifice | % survival |
| Group K | N2 | 22 (23)* | 11 | 50 (47) |
| Group M | N3 | 22 | 13 | 59 |

*One mouse in Group K had to be replaced at the beginning of the study. The data can be analyzed with or without this replacement mouse.

Following sacrifice, mice were dissected and the brainstems and midbrains were homogenized using a potter-type mechanical homogenizer (VOS 14 S40, rate 750 rpm; VWR) in 10 weight-volumes of ice-cold Tris-proteinase-phosphatase-inhibitor buffer (TPPI-buffer) containing: 20 mM Tris-HCl (pH 8.1); 150 Mm NaCl; 1 mM ethylene diamine tetraacetic acid (EDTA, Merck); 1 mM ethylene glycol tetraacetic acid (EGTA, Sigma-Aldrich); 5 mM sodium pyrophosphate (Sigma); 30 mM sodium fluoride (Sigma-Aldrich); 1 mM PMSF (Sigma); 2 mM sodium vanadate (Sigma); 10 mM 1,10-ortho-phenanthrolinemonohydrate (Sigma-Aldrich); 5 μg/ml soya bean trypsin inhibitor; 5 μg/ml pepstatin; and a cocktail of proteinase inhibitors (CPI, Roche Diagnostics GmbH, Germany). Fixed volumes of 140 μl and 100 μl of the brainstem and midbrain homogenates (TotH), respectively, (approximately half of the total volumes) were centrifuged at 136000×g, for 60 min at 4° C.

(TLA-55 rotor, OptimaTMTLX Ultracentrifuge, Beckman Coulter) to generate a Tris-soluble fraction (SF), with the remainder of the total homogenates being stored at −80° C. Due to a limited number of centrifuge holders (N=12), samples were randomized to equilibrate the centrifuge and divide the different treatment groups over the different centrifugation sessions.

The supernatant (S1, also referred to as "soluble fraction" or "SF") was separated from the pellet (P1), aliquoted and stored at −80° C. The P1 pellet was solubilized in 10 weight volumes of a high-salt solution (0.85 M NaCl containing TPPI-buffer) and centrifuged at 20000×g, for 30 min at 4° C. The resulting high-salt pellet (P2) was stored at −80° C. The supernatant (S2) was brought to 1% Sarkosyl with one tenth 10% Sarkosyl and incubated at room temperature for 60 min in a top-over-top rotary tumbler, then centrifuged at 136000×g, for 60 min at 4° C. The Sarkosyl soluble supernatant (S3) was stored at −80° C. and the Sarkosyl insoluble pellet (P3, also referred to as "insoluble fraction" or "IF") was resuspended in 30 μl TPPI buffer and aliquoted. The total homogenate (TotH), Tris-soluble (SF), and Sarkosyl-insoluble (IF) brainstem fractions generated by the fractionation protocol described above were used in subsequent poly-acrylamide gel electrophoresis and Western blotting analyses.

Poly-acrylamide gel electrophoresis and Western blotting. For application of conventional SDS-PAGE and Western blotting, samples were denatured and reduced by incubation at 95° C. for 10 min, then separated on 7.5% Tris-HCl gels (Criterion XT Precast Gel, 26-well comb, 15 μl, 1.0 mm; Biorad). After dry electrotransfer (iBlot™ Invitrogen) to PVDF-membranes (iBlot™ Gel Transfer Stacks, PVDF, Regular, Invitrogen), the membranes were washed in 0.4% PFA for 30 min and then washed in Tris-buffered saline. Next the membranes were incubated in Tris-buffered saline (TBS, pH 7.6) containing 5% (w/v) non-fat dry milk and 0.1% (v/v) Tween-20 for 1 hour. Blots were incubated with various anti-tau primary antibodies overnight, at the working concentrations shown in Table 3. After washing and incubation with an anti-mouse or anti-rabbit HRP-conjugated secondary antibody (goat-anti-mouse or goat-anti-rabbit IgG, DAKO), blots were developed by the ECL detection system (SuperSignal West Femto Maximum Sensitivity Substrate, product 34096, Thermo Scientific). Images were recorded digitally (VisionWorks Acquisition, UVP) with different exposure times, and dedicated software (VisionWorks Analysis, UVP) was used for analysis of the blots. For comparison, an inter-gel reference gel was run with aliquots of four fractions being run on each gel to be compared. Anti-tau primary monoclonal antibodies used for detection included AT100 (phospho-Tau, Thermo Scientific; dilution 1:250), AT8 (phospho-Tau, Thermo Scientific; dilution 1:500), HT7 (pan Tau, Pierce; dilution 1:1000), and 1F5 (epitope unknown to the Testing Facility, Neotope, dilution 3:500). Blots were re-probed with anti-GAPDH (Abcam 9485; dilution 1:2500) as a loading control. Pan Tau antibodies are not specific for phospho-Tau.

TABLE 3

Summary of antibodies used for biochemistry analysis

| mAb | Supplier | Specificity (human) | Stock Conc. | Work Conc. |
|---|---|---|---|---|
| AT100 | Thermo Scientific | Phospho-PHF-tau pSer212/Thr 214 | 200 μg/ml | 0.8 μg/ml |
| AT 8 | Thermo Scientific | Phospho-PHF-tau pSer202/Thr 205 | 200 μg/ml | 0.4 μg/ml |
| HT7 | Pierce | between residue 159 and 163 | 200 μg/ml | 0.2 μg/ml |
| 1F5* | Neotope | $pS^{404}$ | 1 mg/ml | 6 μg/ml |
| GAPDH | Abcam | Human | 1 mg/ml | 0.4 μg/ml |

*IgG2b isotype, JH131-1F5.4.1 hybridoma, lot # NB-0081

Figure 4:
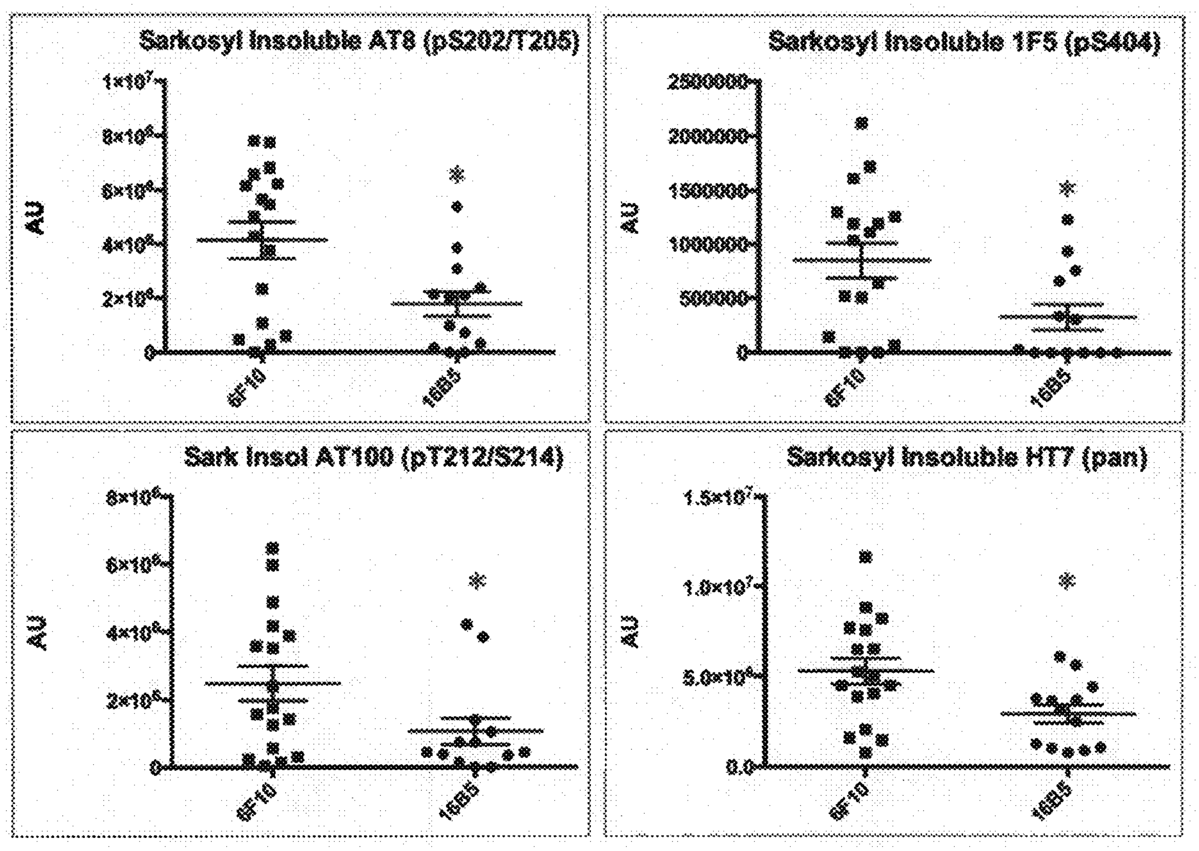
FIG. 4 shows relative amounts of tau protein detected in a sarkosyl insoluble fraction of the brainstem of transgenic mice that express the human tau.P301L protein. The mice were passively immunized with either the 16B5 antibody or the 6F10 antibody, a non-immune IgG1 isotype control. Samples were analyzed by Western blotting, antibody staining, and quantification of the resulting signal. Antibodies used to detect tau included anti-phospho-tau specific antibodies (AT8, upper left panel; AT100, lower left panel; or IF5, upper right panel) and a pan tau antibody (HT7, lower right panel).
Figure 5:
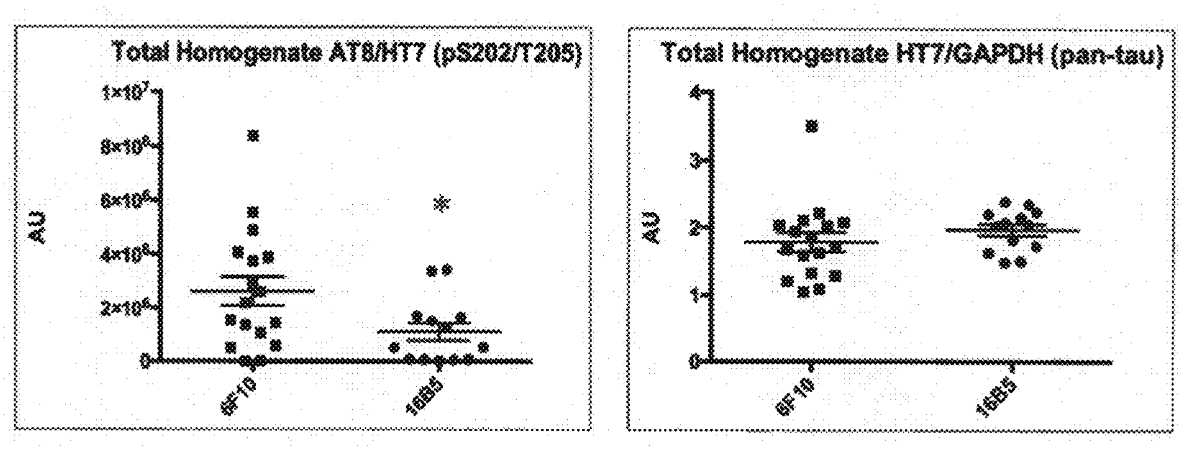
FIG. 5 shows the ratio of phospho-tau to total tau protein (left panel) and a normalized amount of total tau (right panel) detected in total brainstem homogenates of transgenic mice that express the human tau.P301L protein. The mice were passively immunized with either the 16B5 antibody or the 6F10 antibody, a non-immune IgG1 isotype control. Samples were analyzed by Western blotting, antibody staining, and quantification of the resulting signal. The AT8 antibody was used to detect phospho-tau and the HT7 antibody was used to detect total tau. An anti-GAPDH antibody was used to normalize the amount of tau detected in mice treated with the 16B5 antibody versus the control 6F10 antibody.

As shown in FIG. 4, a statistically significant reduction in the amount of tau was observed in sarkosyl insoluble brainstem fractions from animals treated with the 16B5 antibody, as compared to animals treated with the 6F10 control antibody. Statistical significance was assessed using the Student's t test, $p<0.05$. This reduction was observed with both phospho-tau specific antibodies (AT8, upper left-hand panel; AT100, lower left-hand panel; 1F5, upper right-hand panel) and pan-tau antibodies (HT7, lower right-hand panel). Western blots of the total homogenate also indicated a significant reduction in the ratio of phosphor-tau to total tau in the 16B5 treated animals relative to control animals treated with the 6F10 antibody, when detected with a phospho-specific antibody. See FIG. 5, left panel (showing the signal detected with the AT8 anti-phospho-tau antibody divided by the signal detected with the HT7 pan tau antibody). In contrast, there was no significant change in the ratio of total tau to GAPDH levels in the total homogenates of the 16B5 treated animals as compared to the control animals treated with the 6F10 antibody. See FIG. 5, right panel (showing the signal detected with the HT7 pan tau antibody divided by the signal detected with the GAPDH antibody). These data provide evidence that the level of phospho-Tau but not total tau was reduced in the homogenates.)

Histological Analysis. Immuno-histochemical analysis using anti-phospho-tau antibodies was performed in the subthalamic nucleus annex zona incerta (STH/ZI) and the interposed nucleus of the cerebellum, anterior and posterior part, annex lateral cerebellar nucleus (IntA/P/LAT). Sagittal vibratome sections (40 μm) were stored in PBS with 0.1% sodium azide at 4° C. until use. Eight sections per mouse, at bregma indicated, were stained free-floating with mAbs AT8, AT100 or 1F5. Sections were selected for staining with the indicated antibodies as listed in Table 4 below. Sections of all animals selected for a particular staining were randomized for staining and blinded quantification.

Free-floating sections were incubated in Netwells™. Sections were then washed twice in PBS and incubated for 20 minutes in hydrogen peroxide 1.5% in PBS and methanol (1:1) to remove endogenous peroxidase activity. After washing the sections three times in PBS containing 0.1% Triton X100 (PBST), the sections were blocked for 30 min in 10% Fetal Calf Serum (FCS) in PBST followed by an overnight incubation with primary antibodies AT8, AT100 (Thermo scientific), using a concentrations of 0.4 μg/ml and 0.05 μg/ml, respectively, in PBST with 10% FCS. After rinsing, the sections were incubated with goat anti-mouse peroxidase labeled (GAMPO) secondary antibody (DAKO, 1/500 in PBST, 10% FCS) and the signal was developed with 3,3'-diaminobenzidine tetrahydrochloride (DAB, 1 tablet per 10 ml Tris-HCl with 3 μl $H_2O_2$ per 10 ml). Sections were counterstained with Mayer's hematoxylin, dehydrated in five steps (50, 70, 95 and 2×100%) in ethanol and xylene (Merck Eurolab) and mounted in Depex (Depex mounting medium, BDH Laboratory).

TABLE 4

| Summary of antibodies used for immunohistochemical analysis | | | | | |
|---|---|---|---|---|---|
| mAb | Supplier | Specificity | Host | Stock Conc. | Work Conc. |
| AT8 | Thermo | Human | Mouse | 200 | 0.4 μg/ml |
| AT100 | Thermo | Human | Mouse | 200 | 0.05 |

Images were acquired with an Olympus BX41 microscope equipped with a Color view II Olympus camera and analyzed with a computer using AnalySIS Five-Cell^D software. Light intensity and condenser settings for the microscope were kept constant throughout the image acquisition process. All acquired images were subjected to the same computer subroutines to minimize investigator bias. Density slice thresholding was applied uniformly throughout analysis.

The region of interest as defined below was selected for automatic quantification of the staining signal(s). Subthalamic nucleus and zona incerta were delineated by cerebral peduncle ventrally and by white mater dorsally, respectively, as well as on the basis of differences in cell density (sagittal cerebellar sections bregma 1,32-1,92). Interposed nucleus of the cerebellum, anterior and posterior part, and lateral cerebellar nucleus were delineated by white matter and changes in cell density and the third ventricle (sagittal cerebellar sections, bregma 1,92-2,64 for LAT and 0,84-1,8 for IntA/P). For each staining, 6 brain sections containing the STH/ZI and 16 sections containing the IntA/P/LAT per mouse were included in the analysis.

Figure 6:
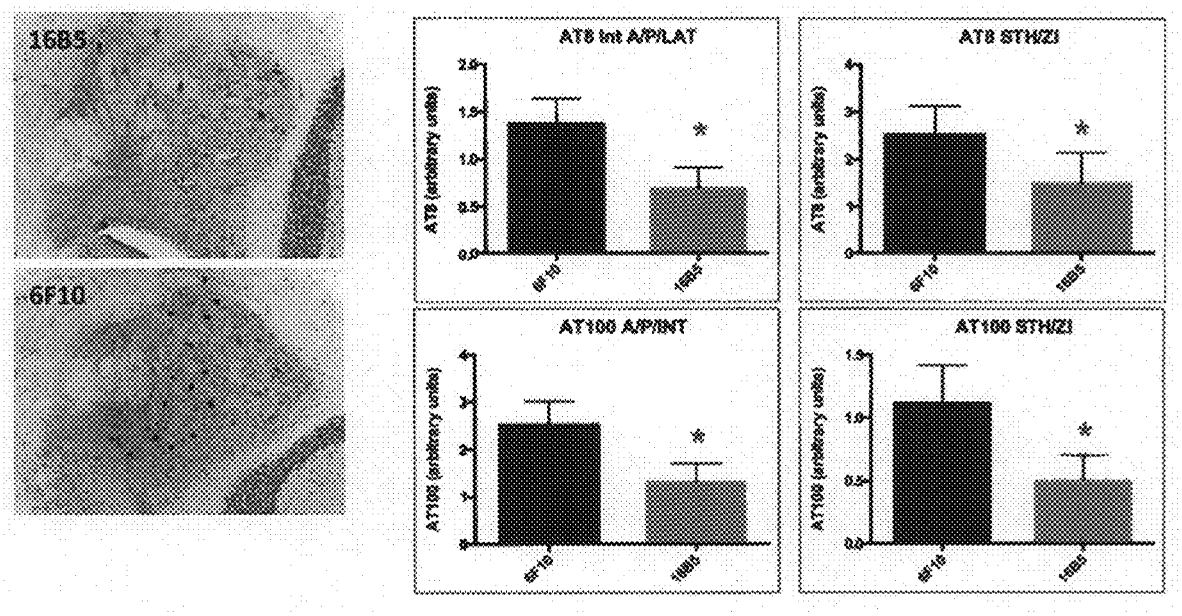
FIG. 6 depicts sections of cerebellar nuclei of transgenic mice that express the human tau.P301L protein, immunohistochemically stained using the AT8 anti-phospho-tau antibody. The mice were passively immunized with either the 16B5 antibody (upper left panel) or the 6F10 antibody (lower left panel), a non-immune IgG1 isotype control. Quantification of the amount of tau staining detected with the AT8 antibody in the interposed nucleus of the cerebellum, anterior and posterior part, annex lateral cerebellar nucleus (IntA/P/LAT) and the subthalamic nucleus annex zona incerta (STH/ZI) from mice passively immunized with 16B5 or 6F10 antibodies is shown in the upper bar graph panels. Quantification of the amount of phospho-tau staining detected using the AT100 anti-phospho-tau antibody on IntA/P/LAT and STH/ZI sections from mice passively immunized with 16B5 or 6F10 antibodies is shown in the lower bar graph panels. Statistical significance was assessed using the Student's t test, $p<0.05$.

As shown in FIG. 6, the amount of phospho-tau detected in the cerebellar nuclei and the subthalamic region of animals treated with the 16B5 antibody was significantly reduced as compared to the amount of phospho-tau detected in the same structures in control animals treated with the 6F10 antibody. Statistical significance was assessed using the Student's t test, $p<0.05$.

Example 5. Humanization of 16B5

Sequence analysis shows that the 16B5 antibody has a variable kappa (Vk) domain having the sequence of SEQ ID NO:16, which belongs to mouse Kabat subgroup 1, and corresponds to human Kabat subgroup 4. Kabat CDRs are underlined. The variable heavy (Vh) domain of the 16B5 antibody has the sequence of SEQ ID NO:10, which belongs to mouse Kabat subgroup 2b, and corresponds to human Kabat subgroup 1 (Kabat et al. (1991), Sequences of Proteins of Immunological Interest, Fifth Edition; NIH Publication No. 91-3242). Kabat CDRs are underlined.

The 16B5 Vk domain includes a 17 residue CDR-L1 sequence (KSSQSLLNSRTRKNYLA, SEQ ID NO: 17), a 7 residue CDR-L2 sequence (WASTRES, SEQ ID NO: 18), and an 8 residue CDR-L3 (KQSYTLRT, SEQ ID NO: 19). The CDR-L1 sequence belongs to canonical class 3, and the CDR-L2 and CDR-L3 sequences belong to class 1 (Martin & Thornton (1996), J. Mol. Biol. 263:800-15).

The 16B5 Vh domain includes a 5 residue CDR-H1 sequence (YHGMD, SEQ ID NO: 11) based on Kabat numbering or a 10 residue CDR-H1 sequence (GYPFTYHGMD, SEQ ID NO: 24) based on combined Kabat and Chothia numbering, a 17 residue CDR-H2 sequence (WINTYSGVPTYADDFKG, SEQ ID NO: 12), and an 8 residue CDR-H3 sequence (RRDFTMDF, SEQ ID NO: 13). The CDR-H1 sequence belongs to canonical class 1 and the CDR-H2 sequence belongs to class 2 (Martin & Thornton (1996), J. Mol. Biol. 263:800-15). The CDR-H3 sequence has no canonical class, but probably has a kinked base according to the rules of Shirai et al. (1999), FEBS Lett. 455:188-97.

The residues at the interface between the Vk and Vh domains are usual residues for these positions in mice.

A search was performed over the protein sequences in the PDB database (Deshpande et al. (2011), J. Virol. 85:1820-33) to find structures which would provide a rough structural model of the 16B5 antibody. The structure of the anti-Cholera toxin antibody Fab fragment Te33 (pdb code 1*ZEA*_H) was used for the VL with a resolution of 1.78 A. It retained the same canonical structure for the loops as 16B5. The Fab crystal structure in the Dsbb-Fab Complex (pdb code 2ZUQ_B) was used to model the VH domain of 16B5. It was solved at a resolution of 3.3 A and contained the same canonical structures for CDR-H1 and CDR-H2, and also the same length CDR-H3 with a kinked based. The BioLuminate program was used to model a rough structure of 16B5 Fv.

A search of the non-redundant protein sequence database from NCBI with a CDR"X"ed 16B5 Fv sequence allowed selection of suitable human frameworks into which to graft the murine CDRs. For Vk, a human kappa light chain with NCBI accession code ACJ71718.pro was chosen (SEQ ID NO:20). This human kappa light chain sequence has the same canonical classes for CDR-L2 and L3. For Vh, human Ig heavy chain BAC02002.1 was chosen (SEQ ID NO:14). It shares the canonical form of 16B5 CDR-H1 and H2, and H3 is 8 residues long with a predicted kinked base.

The humanized heavy chain and light chain designs and backmutations based on these human frameworks are shown in Tables 5 and 6, respectively.

A humanized 16B5 variable heavy chain (H1) having the sequence of SEQ ID NO: 15 was designed. The design includes three backmutations: R13K; V48M; and Y98F. The K at position 13 was selected because it is more frequent than R in humans. The M at position 48 was selected because it is more frequent than V in humans. The F at position 98 was selected because it is located at an interface, making it desirable to keep the mouse residue.

Three humanized 16B5 variable light chain sequences were designed:

Version 1 (L1) has the sequence of SEQ ID NO: 21 and includes three backmutations: DIN; M4L; and Y36F. The N at position 1 was selected because it forms a potential hydrogen bond with N61 in HCDR2. The L at position 4 was selected because it contacts K96, Q97 and S98 in LCDR3; it also contacts F104, an interface residue. The F at position 36 was selected because Y can hydrogen bond with D106 in HCDR3, whereas F cannot. The hydrogen bond would constitute an extra interaction which may affect HCDR3 function, and thus is preferably avoided.

Version 2 (L2) has the sequence of SEQ ID NO: 22 and includes four backmutations: DIN; M4L; Y36F; and P43S. The rationale for DIN, M4L, and Y36F are the same as for Version 1. The S at position 43 was selected because S forms a hydrogen bond with Q110 in VH, which is close to HCDR3.

Version 3 (L3) has the sequence of SEQ ID NO: 23 and includes three backmutations: M4L; Y36F; and P43S. The rationale for each of these mutations is the same as for Versions 1 and 2.

TABLE 5

Sequences for humanization of 16B5 heavy chain

| Kabat residue # | Linear residue # | FR or CDR | Parent mouse mAb SEQ ID NO: 10 | Hu VH Acceptor FR B2 SEQ ID NO: 14 | Humanized Design v1 (R13K, V48M, Y91F) SEQ ID NO: 15 |
|---|---|---|---|---|---|
| 1 | 1 | Fr1 | Q | Q | Q |
| 2 | 2 | Fr1 | I | V | V |
| 3 | 3 | Fr1 | Q | Q | Q |
| 4 | 4 | Fr1 | L | L | L |
| 5 | 5 | Fr1 | V | V | V |
| 6 | 6 | Fr1 | Q | Q | Q |
| 7 | 7 | Fr1 | S | S | S |
| 8 | 8 | Fr1 | G | G | G |
| 9 | 9 | Fr1 | P | S | S |
| 10 | 10 | Fr1 | E | E | E |
| 11 | 11 | Fr1 | L | L | L |
| 12 | 12 | Fr1 | K | K | K |
| 13 | 13 | Fr1 | K | R | K |
| 14 | 14 | Fr1 | P | P | P |
| 15 | 15 | Fr1 | G | G | G |
| 16 | 16 | Fr1 | E | A | A |
| 17 | 17 | Fr1 | T | S | S |
| 18 | 18 | Fr1 | V | V | V |
| 19 | 19 | Fr1 | K | K | K |
| 20 | 20 | Fr1 | I | V | V |
| 21 | 21 | Fr1 | S | S | S |
| 22 | 22 | Fr1 | C | C | C |
| 23 | 23 | Fr1 | K | K | K |
| 24 | 24 | Fr1 | A | A | A |
| 25 | 25 | Fr1 | S | S | S |
| 26 | 26 | Fr1 | G | G | G |
| 27 | 27 | Fr1 | Y | Y | Y |
| 28 | 28 | Fr1 | P | S | T |
| 29 | 29 | Fr1 | F | F | T |
| 30 | 30 | Fr1 | T | T | T |
| 31 | 31 | CDR-H1 | Y | S | Y |
| 32 | 32 | CDR-H1 | H | Y | H |
| 33 | 33 | CDR-H1 | G | A | G |
| 34 | 34 | CDR-H1 | M | V | M |
| 35 | 35 | CDR-H1 | D | N | D |
| 35A | | CDR-H1 | | | |
| 35B | | CDR-H1 | | | |
| 36 | 36 | Fr2 | W | W | W |
| 37 | 37 | Fr2 | V | V | V |
| 38 | 38 | Fr2 | K | R | R |
| 39 | 39 | Fr2 | Q | Q | Q |
| 40 | 40 | Fr2 | A | A | A |
| 41 | 41 | Fr2 | P | P | P |
| 42 | 42 | Fr2 | W | G | G |
| 43 | 43 | Fr2 | G | Q | Q |
| 44 | 44 | Fr2 | G | G | G |
| 45 | 45 | Fr2 | L | L | L |
| 46 | 46 | Fr2 | E | E | E |
| 47 | 47 | Fr2 | W | W | W |
| 48 | 48 | Fr2 | M | V | M |
| 49 | 49 | Fr2 | G | G | G |
| 50 | 50 | CDR-H2 | W | W | W |
| 51 | 51 | CDR-H2 | I | I | I |
| 52 | 52 | CDR-H2 | N | N | N |
| 52A | 53 | CDR-H2 | T | T | T |
| 52B | 54 | CDR-H2 | Y | N | Y |
| 52C | 55 | CDR-H2 | S | T | S |
| 52D | 56 | CDR-H2 | G | G | G |
| 52E | 57 | CDR-H2 | V | N | V |
| 52F | 58 | CDR-H2 | P | P | P |
| 53 | 59 | CDR-H2 | T | T | T |
| 54 | 60 | CDR-H2 | Y | Y | Y |
| 55 | 61 | CDR-H2 | A | A | A |
| 56 | 62 | CDR-H2 | D | Q | D |
| 57 | 63 | CDR-H2 | D | G | D |
| 58 | 64 | CDR-H2 | F | F | F |
| 59 | 65 | CDR-H2 | K | T | K |
| 60 | 66 | CDR-H2 | G | G | G |
| 66 | 67 | Fr3 | R | R | R |
| 67 | 68 | Fr3 | F | F | F |
| 68 | 69 | Fr3 | A | V | V |
| 69 | 70 | Fr3 | F | F | F |
| 70 | 71 | Fr3 | S | S | S |
| 71 | 72 | Fr3 | L | L | L |
| 72 | 73 | Fr3 | E | D | D |
| 73 | 74 | Fr3 | T | T | T |
| 74 | 75 | Fr3 | S | S | S |
| 75 | 76 | Fr3 | V | V | V |
| 76 | 77 | Fr3 | G | S | S |
| 77 | 78 | Fr3 | T | T | T |
| 78 | 79 | Fr3 | A | A | A |
| 79 | 83 | Fr3 | Y | Y | Y |
| 80 | 84 | Fr3 | L | L | L |
| 81 | 85 | Fr3 | Q | Q | Q |
| 82 | 86 | Fr3 | I | I | I |
| 82A | 87 | Fr3 | N | S | S |
| 82B | 88 | Fr3 | N | S | S |
| 82C | 89 | Fr3 | L | L | L |
| 83 | 90 | Fr3 | K | K | K |
| 84 | 91 | Fr3 | N | A | A |
| 85 | 92 | Fr3 | E | A | E |
| 86 | 93 | Fr3 | D | D | D |
| 87 | 94 | Fr3 | T | T | T |
| 88 | 95 | Fr3 | A | A | A |
| 89 | 96 | Fr3 | T | V | V |
| 90 | 97 | Fr3 | Y | Y | Y |
| 91 | 98 | Fr3 | F | Y | F |
| 92 | 99 | Fr3 | C | C | C |
| 93 | 100 | Fr3 | A | A | A |
| 94 | 101 | Fr3 | R | R | R |
| 95 | 102 | CDR-H3 | R | A | R |
| 96 | 103 | CDR-H3 | R | R | R |
| 97 | 104 | CDR-H3 | D | G | D |
| 98 | 105 | CDR-H3 | F | Q | F |
| 99 | 106 | CDR-H3 | T | Z | T |
| 100 | 107 | CDR-H3 | M | G | M |
| 100A | | CDR-H3 | | M | |
| 100B | | | | | |
| 100C | | | | | |
| 100D | | | | | |
| 100E | | | | | |
| 100F | | | | | |
| 100G | | | | | |
| 100H | | | | | |
| 100I | | | | | |
| 100J | | | | | |
| 100K | | | | | |
| 101 | 108 | CDR-H3 | D | D | D |
| 102 | 109 | CDR-H3 | F | V | F |
| 103 | 110 | Fr4 | W | W | W |
| 104 | 111 | Fr4 | G | G | G |
| 105 | 112 | Fr4 | Q | Q | Q |
| 106 | 113 | Fr4 | G | G | G |
| 107 | 114 | Fr4 | T | T | T |
| 108 | 115 | Fr4 | S | T | T |
| 109 | 116 | Fr4 | V | V | V |
| 110 | 117 | Fr4 | T | T | T |
| 111 | 118 | Fr4 | V | V | V |
| 112 | 119 | Fr4 | S | S | S |
| 113 | 120 | Fr4 | S | S | S |

TABLE 6

Sequences of humanized 16B5 light chain variable regions

| Kabat residue # | Linear residue # | FR or CDR | Parent mouse mAb SEQ ID NO: 16 | Hu VL Acceptor Fr SEQ ID NO: 20 | Humanized Design v1 (D1N, M4L, Y36F) SEQ ID NO: 21 | Humanized Design v2 (D1N, M4L, Y36F, P43S) SEQ ID NO: 22 | Humanized Design v3 (M4L, Y36F, P43S) SEQ ID NO: 23 |
|---|---|---|---|---|---|---|---|
| 1 | 1 | Fr1 | N | D | N | N | D |
| 2 | 2 | Fr1 | I | I | I | I | I |
| 3 | 3 | Fr1 | V | V | V | V | V |
| 4 | 4 | Fr1 | L | M | L | L | L |
| 5 | 5 | Fr1 | S | T | T | T | T |
| 6 | 6 | Fr1 | Q | Q | Q | Q | Q |
| 7 | 7 | Fr1 | S | S | S | S | S |
| 8 | 8 | Fr1 | P | P | P | P | P |
| 9 | 9 | Fr1 | S | D | D | D | D |
| 10 | 10 | Fr1 | S | S | S | S | S |
| 11 | 11 | Fr1 | L | L | L | L | L |
| 12 | 12 | Fr1 | A | A | A | A | A |
| 13 | 13 | Fr1 | V | V | V | V | V |
| 14 | 14 | Fr1 | S | S | S | S | S |
| 15 | 15 | Fr1 | P | L | L | L | L |
| 16 | 16 | Fr1 | G | G | G | G | G |
| 17 | 17 | Fr1 | E | E | E | E | E |
| 18 | 18 | Fr1 | K | R | R | R | R |
| 19 | 19 | Fr1 | V | A | A | A | A |
| 20 | 20 | Fr1 | T | T | T | T | T |
| 21 | 21 | Fr1 | M | I | I | I | I |
| 22 | 22 | Fr1 | S | N | N | N | N |
| 23 | 23 | Fr1 | C | C | C | C | C |
| 24 | 24 | CDR-L1 | K | K | K | K | K |
| 25 | 25 | CDR-L1 | S | S | S | S | S |
| 26 | 26 | CDR-L1 | S | S | S | S | S |
| 27 | 27 | CDR-L1 | Q | Q | Q | Q | Q |
| 27A | 28 | CDR-L1 | S | S | S | S | S |
| 27B | 29 | CDR-L1 | L | V | L | L | L |
| 27C | 30 | CDR-L1 | L | L | L | L | L |
| 27D | 31 | CDR-L1 | N | Y | N | N | N |
| 27E | 32 | CDR-L1 | S | S | S | S | S |
| 27F | 33 | CDR-L1 | R | S | R | R | R |
| 28 | 34 | CDR-L1 | T | N | T | T | T |
| 29 | 35 | CDR-L1 | R | N | R | R | R |
| 30 | 36 | CDR-L1 | K | K | K | K | K |
| 31 | 37 | CDR-L1 | N | N | N | N | N |
| 32 | 38 | CDR-L1 | Y | Y | Y | Y | Y |
| 33 | 39 | CDR-L1 | L | L | L | L | L |
| 34 | 40 | CDR-L1 | A | A | A | A | A |
| 35 | 41 | Fr2 | W | W | W | W | W |
| 36 | 42 | Fr2 | F | Y | F | F | F |
| 37 | 43 | Fr2 | Q | Q | Q | Q | Q |
| 38 | 44 | Fr2 | Q | Q | Q | Q | Q |
| 39 | 45 | Fr2 | K | K | K | K | K |
| 40 | 46 | Fr2 | P | P | P | P | P |
| 41 | 47 | Fr2 | G | G | G | G | G |
| 42 | 48 | Fr2 | Q | Q | Q | Q | Q |
| 43 | 49 | Fr2 | S | P | P | S | S |
| 44 | 50 | Fr2 | P | P | P | P | P |
| 45 | 51 | Fr2 | K | K | K | K | K |
| 46 | 52 | Fr2 | L | L | L | L | L |
| 47 | 53 | Fr2 | L | L | L | L | L |
| 48 | 54 | Fr2 | I | I | I | I | I |
| 49 | 55 | Fr2 | Y | Y | Y | Y | Y |
| 50 | 56 | CDR-L2 | W | W | W | W | W |
| 51 | 57 | CDR-L2 | A | A | A | A | A |
| 52 | 58 | CDR-L2 | S | S | S | S | S |
| 53 | 59 | CDR-L2 | T | T | T | T | T |
| 54 | 60 | CDR-L2 | R | R | R | R | R |
| 55 | 61 | CDR-L2 | E | E | E | E | E |
| 56 | 62 | CDR-L2 | S | S | S | S | S |
| 57 | 63 | Fr3 | G | G | G | G | G |
| 58 | 64 | Fr3 | V | V | V | V | V |
| 59 | 65 | Fr3 | P | P | P | P | P |

TABLE 6-continued

Sequences of humanized 16B5 light chain variable regions

| Kabat residue # | Linear residue # | FR or CDR | Parent mouse mAb SEQ ID NO: 16 | Hu VL Acceptor Fr SEQ ID NO: 20 | Humanized Design v1 (D1N, M4L, Y36F) SEQ ID NO: 21 | Humanized Design v2 (D1N, M4L, Y36F, P43S) SEQ ID NO: 22 | Humanized Design v3 (M4L, Y36F, P43S) SEQ ID NO: 23 |
|---|---|---|---|---|---|---|---|
| 60 | 66 | Fr3 | D | D | D | D | D |
| 61 | 67 | Fr3 | R | R | R | R | R |
| 62 | 68 | Fr3 | F | F | F | F | F |
| 63 | 69 | Fr3 | T | S | S | S | S |
| 64 | 70 | Fr3 | G | G | G | G | G |
| 65 | 71 | Fr3 | S | S | S | S | S |
| 66 | 72 | Fr3 | G | G | G | G | G |
| 67 | 73 | Fr3 | S | S | S | S | S |
| 68 | 74 | Fr3 | G | G | G | G | G |
| 69 | 75 | Fr3 | T | T | T | T | T |
| 70 | 76 | Fr3 | D | D | D | D | D |
| 71 | 77 | Fr3 | F | F | F | F | F |
| 72 | 78 | Fr3 | T | T | T | T | T |
| 73 | 79 | Fr3 | L | L | L | L | L |
| 74 | 80 | Fr3 | T | T | T | T | T |
| 75 | 81 | Fr3 | I | I | I | I | I |
| 76 | 82 | Fr3 | S | S | S | S | S |
| 77 | 83 | Fr3 | S | S | S | S | S |
| 78 | 84 | Fr3 | V | L | L | L | L |
| 79 | 85 | Fr3 | Q | Q | Q | Q | Q |
| 80 | 86 | Fr3 | A | A | A | A | A |
| 81 | 87 | Fr3 | E | E | E | E | E |
| 82 | 88 | Fr3 | D | D | D | D | D |
| 83 | 89 | Fr3 | L | V | V | V | V |
| 84 | 90 | Fr3 | A | A | A | A | A |
| 85 | 91 | Fr3 | V | V | V | V | V |
| 86 | 92 | Fr3 | Y | Y | Y | Y | Y |
| 87 | 93 | Fr3 | Y | Y | Y | Y | Y |
| 88 | 94 | Fr3 | C | C | C | C | C |
| 89 | 95 | CDR-L3 | K | Q | K | K | K |
| 90 | 96 | CDR-L3 | Q | Q | Q | Q | Q |
| 91 | 97 | CDR-L3 | S | Y | S | S | S |
| 92 | 98 | CDR-L3 | Y | Y | Y | Y | Y |
| 93 | 99 | CDR-L3 | T | S | T | T | T |
| 94 | 100 | CDR-L3 | L | T | L | L | L |
| 95 | | CDR-L3 | | P | | | |
| 95A | | CDR-L3 | | | | | |
| 95B | | CDR-L3 | | | | | |
| 95C | | CDR-L3 | | | | | |
| 95D | | CDR-L3 | | | | | |
| 95E | | CDR-L3 | | | | | |
| 95F | | CDR-L3 | | | | | |
| 96 | 101 | CDR-L3 | R | Q | R | R | R |
| 97 | 102 | CDR-L3 | T | T | T | T | T |
| 98 | 103 | Fr4 | F | F | F | F | F |
| 99 | 104 | Fr4 | G | G | G | G | G |
| 100 | 105 | Fr4 | G | G | G | G | G |
| 101 | 106 | Fr4 | G | G | G | G | G |
| 102 | 107 | Fr4 | T | T | T | T | T |
| 103 | 108 | Fr4 | N | K | K | K | K |
| 104 | 109 | Fr4 | L | V | V | V | V |
| 105 | 110 | Fr4 | E | E | E | E | E |
| 106 | 111 | Fr4 | I | I | I | I | I |
| 106A | 112 | Fr4 | K | K | K | K | K |
| 107 | 113 | Fr4 | R | R | R | R | R |

Example 6. Tau Affinity of Humanized 16B5 Antibodies

Binding data for humanized 16B5 antibodies having an H1L1 or H1L2 design are shown in Table 7, below. For comparison, the binding data for chimeric 16B5 is also shown. The data was generated using a Biacore instrument. It was concluded that version H1L2 has the strongest affinity—essentially the same as that of chimeric 16B5. Humanized 16B5 versions H1L1 and H1L3 also had adequate affinity.

Surface Plasmon Resonance measurements were performed using a Biacore T200 (GE Lifesciences). All experiments were performed using a mobile phase of 10 mM HEPES pH 7.4, 150 mM NaCl, and 0.05% Tween-20 at 30 μl/min, over a CM5 sensor chip prepared by amine-coupling an anti-mouse or anti-human capture antibody. 16B5 (chimeric or humanized form) was bound to the immobilized capture antibody, and varied concentrations of recombinant purified hTau-P301L were applied to the antibody complex in successive iterations. Iterative steps were separated with high salt or low pH regeneration steps. The experiments were repeated with different preparations of antibody and antigen. Analysis was performed with onboard Biacore software.

TABLE 7

| Biacore Data | | | | | |
|---|---|---|---|---|---|
| | $K_D$ (M) | $K_{on}$ (1/Ms) | $K_{on}$ Error | $K_{off}$ (1/s) | $K_{off}$ Error |
| Chi16B5 | 232 pM | $1.43 \times 10^7$ | $1.5 \times 10^5$ | $3.33 \times 10^{-3}$ | $3.5 \times 10^{-5}$ |
| Hu16B5H1L1 | 617 pM | $3.5 \times 10^6$ | $1.5 \times 10^4$ | $2.15 \times 10^{-3}$ | $8.2 \times 10^{-6}$ |
| Hu16B5H1L2 | 286 pM | $1.2 \times 10^7$ | $4.6 \times 10^4$ | $3.42 \times 10^{-3}$ | $1.1 \times 10^{-5}$ |
| Hu16B5H1L3 | 320 pM | $1.25 \times 10^7$ | $6.2 \times 10^4$ | $3.98 \times 10^{-3}$ | $1.8 \times 10^{-5}$ |

Example 7. Immunoprecipitation Detection of Tau with Humanized 16B5 Antibodies A postmortem sample of frontal cortex from an Alzheimer disease patient with a Braak score of 6 was sequentially extracted in buffers of increasing solubilization strength, in the following order: (i) High salt buffer (20 mM Tris, 5 mM EDTA, 1 mM DTT, 10% sucrose, 7500 mM NaCl pH 7.4), (ii) Triton buffer (20 mM Tris, 5 mM EDTA, 1 mM DTT, 10% sucrose, 1% Triton X100, 500 mM NaCl pH 7.4), and (iii) Sarkosyl Buffer (10 mM Tris, 5 mM EDTA, 1 mM DTT, 10% sucrose, 500 mM NaCl, 1% Sarkosyl, pH 7.4).

For each sample, 200 micrograms of the high salt soluble, or 20 micrograms of the sarkosyl insoluble, fractions were diluted into 400 microliters of immunoprecipitation buffer (10 mM Tris, 150 mM NaCl, 0.5% Triton X100, 1 mM EGTA, 1 mM EDTA, pH 7.4). The samples were precleared with protein G magnetic beads (New England Biolabs), and 5 micrograms of antibody was added to each tube. Antibodies used included: 1) mouse non-immune IgG antibody (mIgG), as control; 2) human non-immune IgG antibody (hIgG), as control; 3) chimeric 16B5 antibody (Chi16B5); 4) humanized 16B5, version H1L2 (h16B6-H1L2); and humanized 16B5, version H1L3 (h16B6-H1L3). Precleared lysates and antibodies were incubated for 2 hours at 4° C. Antibody/antigen complexes were precipitated by using protein G magnetic beads, and the precipitates were washed thoroughly with PBS/350 mM NaCl. After elution using Laemmli buffer, eluates were resolved by SDS-PAGE and blotted using a polyclonal tau antibody (DAKO).

Figure 7:
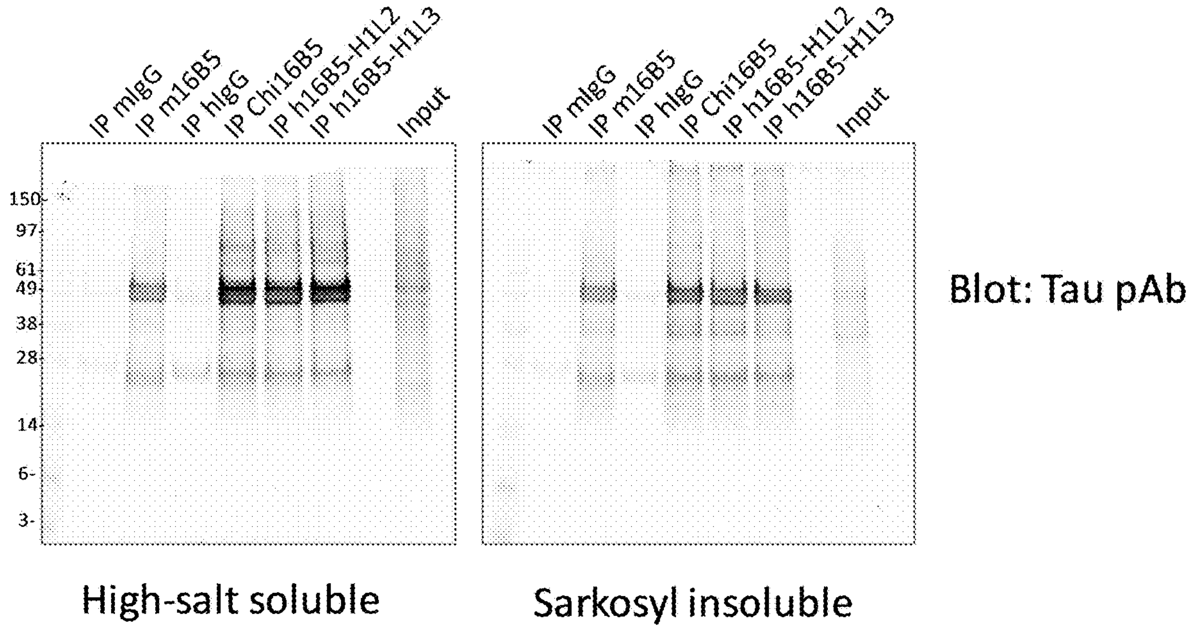
FIG. 7 depicts tau immunoprecipitation results obtained with chimeric 16B5 antibodies and humanized 16B5 antibodies (H1L2 and H1L3 versions). Tau was immunoprecipitated from both soluble and insoluble fractions of postmortem frontal cortex samples obtained from an Alzheimer disease patient. Tau present in blotted immuno-precipitates was detected using a polyclonal anti-tau antibody (tau pAb).

As shown in FIG. 7, chimeric 16B5 and humanized 16B5 H1L2 and H1L3 recognized tau in both soluble and insoluble fractions from Alzheimer's brain.

Example 8. Immunohistochemical Characterization of Murine and Humanized 16B5 Tau Antibodies on Alzheimer's Disease Brain Murine monoclonal anti-tau antibody 16B5 and its two humanized variants, h16B5-H1L2 and h16B5-N1D, were also tested immunohistochemically on fresh frozen sections of human brain cortex from Alzheimer's disease donors and non-diseased, aged controls.

Methods:

Human Brain Tissue

Frontal cortices were obtained from Sun Health Research Institute. Cases included six patients (mean age 86.8±0.40 SEM) diagnosed with Alzheimer's disease and confirmed upon post mortem neuropathological assessment, and three non-diseased aged controls (mean age 77±9.7 SEM). Demographics of the cases are listed in Table 8, below. Immunohistochemistry was performed on lightly acetone-fixed, 10 μm slide-mounted cryosections.

TABLE 8

| Demographics for cases examined immunohistochemically | | | | |
|---|---|---|---|---|
| Case | Diagnosis | Expired Age (years) | Sex | Post-mortem interval (h) |
| 11-21 | AD | 88 | F | 2.28 |
| 03-34 | AD | 88 | F | 3.3 |
| 08-06 | AD | 86 | M | 2.66 |
| 03-52 | AD | 86 | M | 2.2 |
| 01-16 | AD | 87 | M | 3 |
| 01-18 | AD | 86 | M | 3 |
| 10-63 | Control | 79 | M | 3 |
| 10-39 | Control | 93 | M | 3 |
| 10-22 | Control | 59 | F | 3.2 |

Immunohistochemistry

The immunoperoxidase method was the principal detection system, which consisted of either a peroxidase labeled polymer conjugated to goat anti-mouse immunoglobulins (EnVision+System HRP labeled Polymer; Dako K4001) or a Vector ABC amplification system for directly biotinylated humanized antibodies (ABC Elite Standard; PK-6100; Vector Laboratories). The staining was visualized with a DAB chromogen (Liquid DAB+Substrate Chromogen System; Dako K3468), which produced a brown deposit.

The negative control consisted of performing the entire immunohistochemical procedure on adjacent sections with an IgG isotype control antibody or an omission of the primary antibody.

Immunofluorescent Labeling

Double immunofluorescent staining was conducted to determine the relationship between the murine and humanized variants of the antibody, other tau antibodies that recognize various phosphorylated epitopes, and amyloid beta. Tissue sections were stained in parallel with an antibody cocktail containing biotinylated or FITC-tagged humanized 16B5 variants (1 μg/mL) and a murine antibody (either monoclonal 16B5 (1 ug/mL), AT8 (1:1000), AT100 (1:1000), or 3D6 (1 ug/mL). The murine antibodies were detected with a goat anti-mouse secondary conjugated to a 488 or 635 fluorophore (Invitrogen). The biotinylated humanized antibodies were detected with a streptavidin 635.

Preabsorptions

To assess the specificity of the antibodies to its target antigens, 1 ug/mL of 16B5 antibodies were preabsorbed with 50 ug/mL of purified human P301L tau or wild-type synuclein (an irrelevant protein) overnight at 4° C. The antibodies were then applied to tissue and the immunohistochemistry procedure was conducted as outlined above.

Image Analysis

Slides were imaged with either an Olympus BX61 microscope, Olympus Nanozoomer 2.0HT, or a Leica SPE spectral confocal system. Images were collected as TIFF files.

Results

As shown in Table 9, below, mouse monoclonal antibody 16B5 and both humanized variants showed reactivity on Alzheimer's disease tissue, staining prominently neuropil threads, some neurofibrillary tangles (mostly globose), and some tau-positive neuritic plaques. Most of the 16B5 AD-fibrillar pathology were confined to the grey matter, but some reactivity was also detected in the white. The non-diseased control tissue, in contrast, showed diffuse background reactivity but was negative for any pathologies found in the AD tissue.

Double labeling experiments were performed with the murine monoclonal version of 16B5 and with (1) both humanized variants, (2) antibodies recognizing tau at various phosphorylated epitopes, and (3) beta amyloid to further characterize the pathologies recognized by the antibody variants.

Both h16B5-H1L2 and h16B5-N1D colocalized with monoclonal 16B5 antibody with high congruence on AD-fibrillar pathological structures. H16B5-H1L2 also detected pathologies that were shown to be immunoreactive to various phosphorylated tau epitopes, including serine202 and threonine205 (AT8), serine212 and threonine214 (AT100), and serine396 (in-house proprietary antibody, 20H1). Finally, double labeling with an amyloid beta antibody that recognizes the N-terminal amino acid sequence (3D6; aa 1-5) and 16B5 showed very little colocalization between Aβ and 16B5-immunoreactive structures on amyloid plaques.

When 16B5 immunoreactivity was compared to a well characterized commercially available monoclonal anti-tau antibody (Dako), both stained the fibrillar AD pathology which included tau-positive neuritic plaques, neuropil threads, and neurofibrillary tangles.

The specificity of the antibody was assessed by preabsorptions with purified recombinant P301L tau. A decrement in the staining was observed when 16B5 was preabsorbed with P301L tau, but staining was unaffected when the antibodies were preabsorbed with an irrelevant protein (wild-type synuclein) at the same molar concentrations.

Both the IgG-isotype control antibody and primary antibody omission sections were negative for staining across all tissues tested.

TABLE 9

16B5 antibodies characterized immunohistochemically

| Antibody | Lot# | Stain AD Tissue | Concentration |
|---|---|---|---|
| Murine 16B5 | NB-0174A | Yes | 1 ug/mL |
| Chimeric 16B5 | 061512 | Yes | 1 ug/mL |
| h16B5-H1L2 | NB-0248 | Yes | 1 ug/mL |
| H16B5-N1D | 011113 | Yes | 1 ug/mL |

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like, the application refers to the sequences associated with the cited accession numbers as of the effective filing date of the application meaning the actual filing date or earlier date of a priority application disclosing the relevant accession number. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

```
SEQUENCE LISTING
TAU P10636 8
                                                          SEQ ID NO: 1
MAEPRQEFEV MEDHAGTYGL GDRKDQGGYT MHQDQEGDTD AGLKESPLQT TEDGSEEPG

SETSDAKSTP TAEDVTAPLV DEGAPGKQAA AQPHTEIPEG TTAEEAGIGD PSLEDEAAG

HVTQARMVSK SKDGTGSDDK KAKGADGKTK IATPRGAAPP GQKGQANATR PAKTPPAPK

TPPSSGEPPK SGDRSGYSSP GSPGTPGSRS RTPSLPTPPT REPKKVAVVR PPKSPSSAK

SRLQTAPVPM PDLKNVKSKI GSTENLKHQP GGGKVQIINK KLDLSNVQSK GSKDNIKHV

PGGGSVQIVY KPVDLSKVTS KCGSLGNIHH KPGGGQVEVK SEKLDFKDRV SKIGSLDNI

THVPGGGNKK IETHKLTFRE NAKAKTDHGA EIVYKSPVVS GDTSPRHLSN SSTGSIDMV

DSPQLATLAD EVSASLAKQG L

TAU P10636-7
                                                          SEQ ID NO: 2
MAEPRQEFEV MEDHAGTYGL GDRKDQGGYT MHQDQEGDTD AGLKESPLQT TEDGSEEPG

SETSDAKSTP TAEAEEAGIG DTPSLEDEAA GHVTQARMVS KSKDGTGSDD KAKGADGKT

KIATPRGAAP PGQKGQANAT RIPAKTPPAP KTPPSSGEPP KSGDRSGYSS GSPGTPGSR

SRTPSLPTPP TREPKKVAVV RTPPKSPSSA KSRLQTAPVP MPDLKNVKSK GSTENLKHQ

PGGGKVQIIN KKLDLSNVQS KCGSKDNIKH VPGGGSVQIV YKPVDLSKVT KCGSLGNIH

HKPGGGQVEV KSEKLDFKDR VQSKIGSLDN ITHVPGGGNK KIETHKLTFR NAKAKTDHG

AEIVYKSPVV SGDTSPRHLS NVSSTGSIDM VDSPQLATLA DEVSASLAKQ GL

TAU P10636-6
                                                          SEQ ID NO: 3
MAEPRQEFEV MEDHAGTYGL GDRKDQGGYT MHQDQEGDTD AGLKAEEAGI DTPSLEDEA

AGHVTQARMV SKSKDGTGSD DKKAKGADGK TKIATPRGAA PPGQKGQANA RIPAKTPPA
```

-continued

PKTPPSSGEP PKSGDRSGYS SPGSPGTPGS RSRTPSLPTP PTREPKKVAV RTPPKSPSS

AKSRLQTAPV PMPDLKNVKS KIGSTENLKH QPGGGKVQII NKKLDLSNVQ KCGSKDNIK

HVPGGGSVQI VYKPVDLSKV TSKCGSLGNI HHKPGGGQVE VKSEKLDFKD VQSKIGSLD

NITHVPGGGN KKIETHKLTF RENAKAKTDH GAEIVYKSPV VSGDTSPRHL NVSSTGSID

MVDSPQLATL ADEVSASLAK QGL

TAU P10636-5

SEQ ID NO: 4

MAEPRQEFEV MEDHAGTYGL GDRKDQGGYT MHQDQEGDTD AGLKESPLQT TEDGSEEPG

SETSDAKSTP TAEDVTAPLV DEGAPGKQAA AQPHTEIPEG TTAEEAGIGD PSLEDEAAG

HVTQARMVSK SKDGTGSDDK KAKGADGKTK IATPRGAAPP GQKGQANATR PAKTPPAPK

TPPSSGEPPK SGDRSGYSSP GSPGTPGSRS RTPSLPTPPT REPKKVAVVR PPKSPSSAK

SRLQTAPVPM PDLKNVKSKI GSTENLKHQP GGGKVQIVYK PVDLSKVTSK GSLGNIHHK

PGGGQVEVKS EKLDFKDRVQ SKIGSLDNIT HVPGGGNKKI ETHKLTFREN KAKTDHGAE

IVYKSPVVSG DTSPRHLSNV SSTGSIDMVD SPQLATLADE VSASLAKQGL

TAU P10636-4

SEQ ID NO: 5

MAEPRQEFEV MEDHAGTYGL GDRKDQGGYT MHQDQEGDTD AGLKESPLQT TEDGSEEPG

SETSDAKSTP TAEAEEAGIG DTPSLEDEAA GHVTQARMVS KSKDGTGSDD KAKGADGKT

KIATPRGAAP PGQKGQANAT RIPAKTPPAP KTPPSSGEPP KSGDRSGYSS GSPGTPGSR

SRTPSLPTPP TREPKKVAVV RTPPKSPSSA KSRLQTAPVP MPDLKNVKSK GSTENLKHQ

PGGGKVQIVY KPVDLSKVTS KCGSLGNIHH KPGGGQVEVK SEKLDFKDRV SKIGSLDNI

THVPGGGNKK IETHKLTFRE NAKAKTDHGA EIVYKSPVVS GDTSPRHLSN SSTGSIDMV

DSPQLATLAD EVSASLAKQG L

TAU P10636-2

SEQ ID NO: 6

MAEPRQEFEV MEDHAGTYGL GDRKDQGGYT MHQDQEGDTD AGLKAEEAGI GDTPSLEDE

AAGHVTQARM VSKSKDGTGS DDKKAKGADG KTKIATPRGA APPGQKGQAN ATRIPAKTP

PAPKTPPSSG EPPKSGDRSG YSSPGSPGTP GSRSRTPSLP TPPTREPKKV AVVRTPPKS

PSSAKSRLQT APVPMPDLKN VKSKIGSTEN LKHQPGGGKV QIVYKPVDLS KVTSKCGSL

GNIHHKPGGG QVEVKSEKLD FKDRVQSKIG SLDNITHVPG GGNKKIETHK LTFRENAKA

KTDHGAEIVY KSPVVSGDTS PRHLSNVSST GSIDMVDSPQ LATLADEVSA SLAKQGL

SEQ ID NO: 7

CTA ATA CGA CTC ACT ATA GGG C

SEQ ID NO: 8

CTC AAT TTT CTT GTC CAC CTT GGT GC

SEQ ID NO: 9

CTC AAG TTT TTT GTC CAC CGT GGT GC

16B5-HC

SEQ ID NO: 10

MDWVWNLLFLMAAAQSIQAQIQLVQSGPELKKPGETVKISCKASGYPFTYHGMDWVKQAPWGGL

EWMGWINTYSGVPTYADDFKGRFAFSLETSVGTAYLQINNLKNEDTATYFCARRRDFTMDFWGQ

GTSVTVSSAKTTPPSVYPLAPGSAAQTNSMVTLGCLVKGYFPEPVTVTWNSGSLSSGVHTFPAV

LQSDLYTLSSSVTVPSSTWPSETVTCNVAHPAS

-continued

16B5 CDR-H1 (Kabat numbering)
SEQ ID NO: 11
YHGMD

16B5 CDR-H2
SEQ ID NO: 12
WINTYSGVPTYADDFKG

16B5 CDR-H3
SEQ ID NO: 13
RRDFTMDF

Hu VH AcceptQr FR (Acc#BAC02002.1)
SEQ ID NO: 14
QVQLVQSGSELKRPGASVKVSCKASGYSFTSYAVNWVRQAPGQGLEWVGWINTNTGNPTYAQGF

TGRFVFSLDTSVSTAYLQISSLKAADTAVYYCARARGQNGMDVWGQGTTVTVSS

16B5 Heavy Chain Humanized Design v1 (R13K, V48M, Y91F)
SEQ ID NO: 15
KGRFVFSLDTSVSTAYLQISSLKAEDTAVYFCARRRDFTMDFWGQGTTVTVSS 16B5-LC
SEQ ID NO: 16
MDSQAQVLILLLLWVSGTCGNIVLSQSPSSLAVSPGEKVTMSCKSSQSLLNSRTRKNYLAWFQQ

KPGQSPKLLIYWASTRESGVPDRFTGSGSGTDFTLTISSVQAEDLAVYYCKQSYTLRTFGGGTN

LEIKRADAAPTVSIFPPSSEQLTSGGASVVCFLNNFYPKDINVKWKIDGSERQNGVLNSWTDQD

SKDSTYSMSSTLTLTKDEYERHNSYTCEATHKTSTSPI

16B5-LC CDR-L1
SEQ ID NO: 17
KSSQSLLNSRTRKNYLA

16B5-LC CDR-L2
SEQ ID NO: 18
WASTRES

16B5-LC CDR-L3
SEQ ID NO: 19
KQSYTLRT

Hu VL AcceptQr Fr (Acc#ACJ71718.1)
SEQ ID NO: 20
DIVMTQSPDSLAVSLGERATINCKSSQSVLYSSNNKNYLAWYQQKPGQPPKLLIYWASTRESGV

PDRFSGSGSGTDFTLTISSLQAEDVAVYYCQQYYSTPQTFGGGTKVEIKR

16B5 Light Chain Humanized Design v1 (DIN, M4L, Y36F)
SEQ ID NO: 21
NIVLTQSPDSLAVSLGERATINCKSSQSLLNSRTRKNYLAWFQQKPGQPPKLLIYWASTRESGV

PDRFSGSGSGTDFTLTISSLQAEDVAVYYCKQSYTLRTFGGGTKVEIKR

16B5 Light Chain Humanized Design v2 (DIN, M4L, Y36F, P43S)
SEQ ID NO: 22
NIVLTQSPDSLAVSLGERATINCKSSQSLLNSRTRKNYLAWFQQKPGQSPKLLIYWASTRESGV

PDRFSGSGSGTDFTLTISSLQAEDVAVYYCKQSYTLRTFGGGTKVEIKR

16B5 Light Chain Humanized Design v3 (M4L, Y36F, P43S)
SEQ ID NO: 23
DIVLTQSPDSLAVSLGERATINCKSSQSLLNSRTRKNYLAWFQQKPGQSPKLLIYWASTRESGV

PDRFSGSGSGTDFTLTISSLQAEDVAVYYCKQSYTLRTFGGGTKVEIKR

16B5 CDR-H1 (CQmbined Kabat AND Chothia numbering)
SEQ ID NO: 24
GYPFTYHGMD

Nucleic acid encQding 16B5 Heavy Chain Humanized Design v1
SEQ ID NO: 25
CAGgTCCAGTTGGTGCAGTCTGGATCTGAGCTGAAGAAGCCTGGAGCCTCCGTCAAGgtgTCCT GCAAGGCTTCTGGGTATCCCTTCACATACCATGGAATGGACTGGGTGcgtCAGGCTCCTggtca GGGTttaGAGTGGATGGGCTGGATAAACACCTACTCTGGAGTGCCAACATATGCTGATGACTTC -continued AAGGGACGATTTGtgTTCTCTTTGGAcACCTCTGTCtctACTGCCTATTTGCAGATCtcttctC TCAAAgccGAGGACacgGCCgtgTATTTTTGTGCAAGACGGCGTGATTTTACAATGGACTTCTG

GGGTCAAGGAACCACCGTGACCGTCTCCTCA

Nucleic acid encQding 16B5 Light Chain Humanized Design v1

SEQ ID NO: 26

AACATCGTGCTGACCCAGAGCCCCGATAGCCTGGCCGTGAGCCTGGGCGAGAGAGCCACCATCA

ACTGCAAGAGCAGCCAGAGCCTGCTGAACAGCAGGACCAGGAAGAACTACCTGGCCTGGTTCCA

GCAGAAGCCCGGCCAGCCCCCCAAGCTGCTGATCTACTGGGCCAGCACCAGGGAGAGCGGCGTG

CCCGATAGGTTCAGCGGCAGCGGCAGCGGCACCGATTTCACCCTGACCATCAGCAGCCTGCAGG

CCGAGGATGTGGCCGTGTACTACTGCAAGCAGAGCTACACCCTGAGAACCTTCGGCGGCGGCAC

CAAGGTGGAAATTAAACGT

Nucleic acid encoding 16B5 Light Chain Humanized Design v2

SEQ ID NO: 27

AACATCGTGCTGACCCAGAGCCCCGATAGCCTGGCCGTGAGCCTGGGCGAGAGAGCCACCATCA

ACTGCAAGAGCAGCCAGAGCCTGCTGAACAGCAGGACCAGGAAGAACTACCTGGCCTGGTTCCA

GCAGAAGCCCGGCCAGAGCCCCAAGCTGCTGATCTACTGGGCCAGCACCAGGGAGAGCGGCGTG

CCCGATAGGTTCAGCGGCAGCGGCAGCGGCACCGATTTCACCCTGACCATCAGCAGCCTGCAGG

CCGAGGATGTGGCCGTGTACTACTGCAAGCAGAGCTACACCCTGAGAACCTTCGGCGGCGGCAC

CAAGGTGGAAATTAAACGT

Nucleic acid encoding 16B5 Light Chain Humanized Design v3

SEQ ID NO: 28

GACATCGTGCTGACCCAGAGCCCCGATAGCCTGGCCGTGAGCCTGGGCGAGAGAGCCACCATCA

ACTGCAAGAGCAGCCAGAGCCTGCTGAACAGCAGGACCAGGAAGAACTACCTGGCCTGGTTCCA

GCAGAAGCCCGGCCAGAGCCCCAAGCTGCTGATCTACTGGGCCAGCACCAGGGAGAGCGGCGTG

CCCGATAGGTTCAGCGGCAGCGGCAGCGGCACCGATTTCACCCTGACCATCAGCAGCCTGCAGG

CCGAGGATGTGGCCGTGTACTACTGCAAGCAGAGCTACACCCTGAGAACCTTCGGCGGCGGCAC

CAAGGTGGAAATTAAACGT

Human IgG1 constant region (C-terminal lysine can be omitted)

SEQ ID NO: 29

ASTKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKRVEPKSCDKTHTCPPCPAPELLGGPSVFLFPP

KPKDTLMISRTPEVTCVVVDVSHEDPEVKFNWYVDGVEVHNVKTKPREEQYNSTYRVVSVLTVL

HQDWLNGKEYKCKVSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFSCSVMHEALHNHYT

QKSLSLSPGK

Human IgG1 constant region cDNA

SEQ ID NO: 30

GCTAGCACCAAGGGCCCATCGGTCTTCCCCCTGGCACCCTCCTCCAAGAGCACCTCTGGGGGCA

CAGCGGCCCTGGGCTGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGA

ATCACAAGCCCAGCAACACCAAGGTGGACAAGAAAGTTGAGCCCAAATCTTGTGACAAAACTCA

CACATGCCCACCGTGCCCAGCACCTGAACTCCTGGGGGGACCGTCAGTCTTCCTCTTCCCCCCA

-continued

AAACCCAAGGACACCCTCATGATCTCCCGGACCCCTGAGGTCACATGCGTGGTGGTGGACGTGA

GCCACGAAGACCCTGAGGTCAAGTTCAACTGGTACGTGGACGGCGTGGAGGTGCATAATGCCAA

GACAAAGCCGCGGGAGGAGCAGTACAACAGCACGTACCGTGTGGTCAGCGTCCTCACCGTCCTG

CACCAGGACTGGCTGAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAGGTGTACACCCTGCC

CCCATCCCGGGAGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACAAGACCACGC

CTCCCGTGCTGGACTCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGCACAACCACTACACG

CAGAAGAGCCTCTCCCTGTCTCCGGGTAAA

Human IgG1 constant region cDNA with 5' intron

SEQ ID NO: 31

GGTGAGTGGATCCGCGGCCGCTAAACTCTGAGGGGGTCGGATGACGTGGCCATTCTTTGCCTAA

AGCATTGAGTTTACTGCAAGGTCAGAAAAGCATGCAAAGCCCTCAGAATGGCTGCAAAGAGCTC

CAACAAAACAATTTAGAACTTTATTAAGGAATAGGGGGAAGCTAGGAAGAAACTCAAAACATCA

AGATTTTAAATACGCTTCTTGGTCTCCTTGCTATAATTATCTGGGATAAGCATGCTGTTTTCTG

TCTGTCCCTAACATGCCCTGTGATTATCCGCAAACAACACACCCAAGGGCAGAACTTTGTTACT

TAAACACCATCCTGTTTGCTTCTTTCCTCAGCCTCCACCAAGGGCCCATCGGTCTTCCCCCTGG

CACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTGGACAAGAG

AGTTGAGCCCAAATCTTGTGACAAAACTCACACATGCCCACCGTGCCCAGCACCTGAACTCCTG

GGGGGACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCCAAAGCCAAAGGGCA

GCCCCGAGAACCACAGGTGTACACGCTGCCCCCATCCCGGGAGGAGATGACCAAGAACCAGGTC

AGCCTGACCTGCCTGGTCAAAGGCTTCTATCCCAGCGACATCGCCGTGGAGTGGGAGAGCAATG

GGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCCCCGGGTAAATGA

Human kappa constant region

SEQ ID NO: 32

TVAAPSVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC

Human kappa constant region cDNA

SEQ ID NO: 33

ACGGTGGCTGCACCATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTACAGTGGAAGGTGGA

TAACGCCCTCCAATCGGGTAACTCCCAGGAGAGTGTCACAGAGCAGGACAGCAAGGACAGCACC

TACAGCCTCAGCAGCACCCTGACGCTGAGCAAAGCAGACTACGAGAAACACAAAGTCTACGCCT

GCGAAGTCACCCATCAGGGCCTGAGCTCGCCCGTCACAAAGAGCTTCAACAGGGGAGAGTGT

-continued

Human kappa constant region cDNA with 5' intron

SEQ ID NO: 34

CGTGAGTGGATCCGCGGCCGCTAAACTCTGAGGGGGTCGGATGACGTGGCCATTCTTTGCCTAA

AGCATTGAGTTTACTGCAAGGTCAGAAAAGCATGCAAAGCCCTCAGAATGGCTGCAAAGAGCTC

CAACAAAACAATTTAGAACTTTATTAAGGAATAGGGGGAAGCTAGGAAGAAACTCAAAACATCA

AGATTTTAAATACGCTTCTTGGTCTCCTTGCTATAATTATCTGGGATAAGCATGCTGTTTTCTG

TCTGTCCCTAACATGCCCTGTGATTATCCGCAAACAACACACCCAAGGGCAGAACTTTGTTACT

TAAACACCATCCTGTTTGCTTCTTTCCTCAGGAACTGTGGCTGCACCATCTGTCTTCATCTTCC

CGCCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGGAG

AGTGTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTCGCC

CGTCACAAAGAGCTTCAACAGGGGAGAGTGT

What is claimed is:

1. A method of treating or effecting prophylaxis of a disease associated with tau comprising administering an effective regime of a humanized antibody that specifically binds to an epitope within residues 24-46 of SEQ ID NO: 1 (Swiss-Prot No. P10636-8) to a patient having or at risk developing of the disease, wherein the humanized antibody comprises a CDR-H1 comprising SEQ ID NO: 11, a CDR-H2 comprising SEQ ID NO: 12, a CDR-H3 comprising SEQ ID NO: 13, a CDR-L1 comprising SEQ ID NO: 17, a CDR-L2 comprising SEQ ID NO: 18, and a CDR-L3 comprising SEQ ID NO: 19.

2. The method of claim 1, wherein the humanized antibody comprises a humanized mature heavy chain variable region comprising an amino acid sequence at least 90% identical to SEQ ID NO: 15 and a humanized mature light chain variable region comprising an amino acid sequence at least 90% identical to SEQ ID NO: 22.

3. The method of claim 2, wherein at least one of Kabat positions H13, H48, and H91 of the humanized antibody is occupied by K, M, and F, respectively, and at least one of Kabat positions L1, L4, L36, and L43 of the humanized antibody is occupied by N, L, F, and S, respectively.

4. The method of claim 1, wherein the humanized antibody comprises a humanized mature heavy chain variable region comprising an amino acid sequence at least 95% identical to SEQ ID NO: 15 and a humanized mature light chain variable region comprising an amino acid sequence at least 95% identical to SEQ ID NO: 22.

5. The method of claim 1, wherein the humanized antibody comprises a humanized mature heavy chain variable region comprising an amino acid sequence at least 99% identical to SEQ ID NO: 15 and a humanized mature light chain variable region comprising an amino acid sequence at least 99% identical to SEQ ID NO: 22.

6. The method of claim 1, wherein the disease is Alzheimer's disease.

7. A method of reducing aberrant transmission of tau comprising administering an effective regime of a humanized antibody that specifically binds to an epitope within residues 24-46 of SEQ ID NO: 1 (Swiss-Prot No. P10636-8) to a patient having or at risk of a disease associated with aberrant transmission of tau, wherein the humanized antibody comprises a CDR-H1 comprising SEQ ID NO: 11, a CDR-H2 comprising SEQ ID NO: 12, a CDR-H3 comprising SEQ ID NO: 13, a CDR-L1 comprising SEQ ID NO: 17, a CDR-L2 comprising SEQ ID NO: 18, and a CDR-L3 comprising SEQ ID NO: 19.

8. A method of inducing phagocytosis of tau comprising administering an effective regime of a humanized antibody that specifically binds to an epitope within residues 24-46 of SEQ ID NO: 1 (Swiss-Prot No. P10636-8) to a patient having or at risk of a disease associated with the accumulation of tau, wherein the humanized antibody comprises a CDR-H1 comprising SEQ ID NO: 11, a CDR-H2 comprising SEQ ID NO: 12, a CDR-H3 comprising SEQ ID NO: 13, a CDR-L1 comprising SEQ ID NO: 17, a CDR-L2 comprising SEQ ID NO: 18, and a CDR-L3 comprising SEQ ID NO: 19.

9. A method of inhibiting tau aggregation or deposition comprising administering an effective regime of a humanized antibody that specifically binds to an epitope within residues 24-46 of SEQ ID NO: 1 (Swiss-Prot No. P10636-8) to a patient having or at risk of a disease associated with the aggregation or deposition of tau, wherein the humanized antibody comprises a CDR-H1 comprising SEQ ID NO: 11, a CDR-H2 comprising SEQ ID NO: 12, a CDR-H3 comprising SEQ ID NO: 13, a CDR-L1 comprising SEQ ID NO: 17, a CDR-L2 comprising SEQ ID NO: 18, and a CDR-L3 comprising SEQ ID NO: 19.

10. A method of inhibiting formation of tau tangles comprising administering an effective regime of a humanized antibody that specifically binds to an epitope within residues 24-46 of SEQ ID NO: 1 (Swiss-Prot No. P10636-8), to a patient having or at risk of a disease associated with the formation of tau tangles, wherein the humanized antibody comprises a CDR-H1 comprising SEQ ID NO: 11, a CDR-H2 comprising SEQ ID NO: 12, a CDR-H3 comprising SEQ ID NO: 13, a CDR-L1 comprising SEQ ID NO: 17, a CDR-L2 comprising SEQ ID NO: 18, and a CDR-L3 comprising SEQ ID NO: 19.

11. The method of claim 7, wherein the humanized antibody comprises a humanized mature heavy chain variable region comprising an amino acid sequence at least 90% identical to SEQ ID NO: 15 and a mature light chain variable region comprising an amino acid sequence at least 90% identical to SEQ ID NO: 22.

12. The method of claim 11, wherein at least one of Kabat positions H13, H48, and H91 of the humanized antibody is occupied by K, M, and F, respectively, and at least one of Kabat positions L1, L4, L36, and L43 of the humanized antibody is occupied by N, L, F, and S, respectively.

13. The method of claim 7, wherein the humanized antibody comprises a humanized mature heavy chain variable region comprising an amino acid sequence at least 95% identical to SEQ ID NO: 15 and a humanized mature light chain variable region comprising an amino acid sequence at least 95% identical to SEQ ID NO: 22.

14. The method of claim 7, wherein the humanized antibody comprises a humanized mature heavy chain variable region comprising an amino acid sequence at least 99% identical to SEQ ID NO: 15 and a humanized mature light chain variable region comprising an amino acid sequence at least 99% identical to SEQ ID NO: 22.

15. The method of claim 7, wherein the disease is Alzheimer's disease.

16. The method of claim 8, wherein the humanized antibody comprises a humanized mature heavy chain variable region comprising an amino acid sequence at least 90% identical to SEQ ID NO: 15 and a mature light chain variable region comprising an amino acid sequence at least 90% identical to SEQ ID NO: 22.

17. The method of claim 16, wherein at least one of Kabat positions H13, H48, and H91 of the humanized antibody is occupied by K, M, and F, respectively, and at least one of Kabat positions L1, L4, L36, and L43 of the humanized antibody is occupied by N, L, F, and S, respectively.

18. The method of claim 8, wherein the humanized antibody comprises a humanized mature heavy chain variable region comprising an amino acid sequence at least 95% identical to SEQ ID NO: 15 and a humanized mature light chain variable region comprising an amino acid sequence at least 95% identical to SEQ ID NO: 22.

19. The method of claim 8, wherein the humanized antibody comprises a humanized mature heavy chain variable region comprising an amino acid sequence at least 99% identical to SEQ ID NO: 15 and a humanized mature light chain variable region comprising an amino acid sequence at least 99% identical to SEQ ID NO: 22.

20. The method of claim 8, wherein the disease is Alzheimer's disease.

21. The method of claim 9, wherein the humanized antibody comprises a humanized mature heavy chain variable region comprising an amino acid sequence at least 90% identical to SEQ ID NO: 15 and a mature light chain variable region comprising an amino acid sequence at least 90% identical to SEQ ID NO: 22.

22. The method of claim 21, wherein at least one of Kabat positions H13, H48, and H91 of the humanized antibody is occupied by K, M, and F, respectively, and at least one of Kabat positions L1, L4, L36, and L43 of the humanized antibody is occupied by N, L, F, and S, respectively.

23. The method of claim 9, wherein the humanized antibody comprises a humanized mature heavy chain variable region comprising an amino acid sequence at least 95% identical to SEQ ID NO: 15 and a humanized mature light chain variable region comprising an amino acid sequence at least 95% identical to SEQ ID NO: 22.

24. The method of claim 9, wherein the humanized antibody comprises a humanized mature heavy chain variable region comprising an amino acid sequence at least 99% identical to SEQ ID NO: 15 and a humanized mature light chain variable region comprising an amino acid sequence at least 99% identical to SEQ ID NO: 22.

25. The method of claim 9, wherein the disease is Alzheimer's disease.

26. The method of claim 10, wherein the humanized antibody comprises a humanized mature heavy chain variable region comprising an amino acid sequence at least 90% identical to SEQ ID NO: 15 and a mature light chain variable region comprising an amino acid sequence at least 90% identical to SEQ ID NO: 22.

27. The method of claim 26, wherein at least one of Kabat positions H13, H48, and H91 of the humanized antibody is occupied by K, M, and F, respectively, and at least one of Kabat positions L1, L4, L36, and L43 of the humanized antibody is occupied by N, L, F, and S, respectively.

28. The method of claim 10, wherein the humanized antibody comprises a humanized mature heavy chain variable region comprising an amino acid sequence at least 95% identical to SEQ ID NO: 15 and a humanized mature light chain variable region comprising an amino acid sequence at least 95% identical to SEQ ID NO: 22.

29. The method of claim 10, wherein the humanized antibody comprises a humanized mature heavy chain variable region comprising an amino acid sequence at least 99% identical to SEQ ID NO: 15 and a humanized mature light chain variable region comprising an amino acid sequence at least 99% identical to SEQ ID NO: 22.

30. The method of claim 10, wherein the disease is Alzheimer's disease.

* * * * *

SEQUENCE LISTING

```
Sequence total quantity: 34
SEQ ID NO: 1            moltype = AA  length = 441
FEATURE                 Location/Qualifiers
source                  1..441
                        mol_type = protein
                        organism = Homo sapiens
SEQUENCE: 1
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIINK KLDLSNVQSK CGSKDNIKHV  300
PGGGSVQIVY KPVDLSKVTS KCGSLGNIHH KPGGGQVEVK SEKLDFKDRV QSKIGSLDNI  360
THVPGGGNKK IETHKLTFRE NAKAKTDHGA EIVYKSPVVS GDTSPRHLSN VSSTGSIDMV  420
DSPQLATLAD EVSASLAKQG L                                           441

SEQ ID NO: 2            moltype = AA  length = 412
FEATURE                 Location/Qualifiers
source                  1..412
                        mol_type = protein
                        organism = Homo sapiens
SEQUENCE: 2
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT  120
KIATPRGAAP PGQKGQANAT RIPAKTPPAP KTPPSSGEPP KSGDRSGYSS PGSPGTPGSR  180
SRTPSLPTPP TREPKKVAVV RTPPKSPSSA KSRLQTAPVP MPDLKNVKSK IGSTENLKHQ  240
PGGGKVQIIN KKLDLSNVQS KCGSKDNIKH VPGGGSVQIV YKPVDLSKVT SKCGSLGNIH  300
HKPGGGQVEV KSEKLDFKDR VQSKIGSLDN ITHVPGGGNK KIETHKLTFR ENAKAKTDHG  360
AEIVYKSPVV SGDTSPRHLS NVSSTGSIDM VDSPQLATLA DEVSASLAKQ GL          412

SEQ ID NO: 3            moltype = AA  length = 383
FEATURE                 Location/Qualifiers
source                  1..383
                        mol_type = protein
                        organism = Homo sapiens
SEQUENCE: 3
MAEPRQEFEV MEDHAGTYGL GDRKDQGGYT MHQDQEGDTD AGLKAEEAGI GDTPSLEDEA  60
AGHVTQARMV SKSKDGTGSD DKKAKGADGK TKIATPRGAA PPGQKGQANA TRIPAKTPPA  120
PKTPPSSGEP PKSGDRSGYS SPGSPGTPGS RSRTPSLPTP PTREPKKVAV VRTPPKSPSS  180
AKSRLQTAPV PMPDLKNVKS KIGSTENLKH QPGGGKVQII NKKLDLSNVQ SKCGSKDNIK  240
HVPGGGSVQI VYKPVDLSKV TSKCGSLGNI HHKPGGGQVE VKSEKLDFKD RVQSKIGSLD  300
NITHVPGGGN KKIETHKLTF RENAKAKTDH GAEIVYKSPV VSGDTSPRHL SNVSSTGSID  360
MVDSPQLATL ADEVSASLAK QGL                                         383

SEQ ID NO: 4            moltype = AA  length = 410
FEATURE                 Location/Qualifiers
source                  1..410
                        mol_type = protein
                        organism = Homo sapiens
SEQUENCE: 4
```

```
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIVYK PVDLSKVTSK CGSLGNIHHK  300
PGGGQVEVKS EKLDFKDRVQ SKIGSLDNIT HVPGGGNKKI ETHKLTFREN AKAKTDHGAE  360
IVYKSPVVSG DTSPRHLSNV SSTGSIDMVD SPQLATLADE VSASLAKQGL             410

SEQ ID NO: 5            moltype = AA  length = 381
FEATURE                 Location/Qualifiers
source                  1..381
                        mol_type = protein
                        organism = Homo sapiens
SEQUENCE: 5
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT  120
KIATPRGAAP PGQKGQANAT RIPAKTPPAP KTPPSSGEPP KSGDRSGYSS PGSPGTPGSR  180
SRTPSLPTPP TREPKKVAVV RTPPKSPSSA KSRLQTAPVP MPDLKNVKSK IGSTENLKHQ  240
PGGGKVQIVY KPVDLSKVTS KCGSLGNIHH KPGGGQVEVK SEKLDFKDRV QSKIGSLDNI  300
THVPGGGNKK IETHKLTFRE NAKAKTDHGA EIVYKSPVVS GDTSPRHLSN VSSTGSIDMV  360
DSPQLATLAD EVSASLAKQG L                                            381

SEQ ID NO: 6            moltype = AA  length = 352
FEATURE                 Location/Qualifiers
source                  1..352
                        mol_type = protein
                        organism = Homo sapiens
SEQUENCE: 6
MAEPRQEFEV MEDHAGTYGL GDRKDQGGYT MHQDQEGDTD AGLKAEEAGI GDTPSLEDEA  60
AGHVTQARMV SKSKDGTGSD DKKAKGADGK TKIATPRGAA PPGQKGQANA TRIPAKTPPA  120
PKTPPSSGEP PKSGDRSGYS SPGSPGTPGS RSRTPSLPTP PTREPKKVAV VRTPPKSPSS  180
AKSRLQTAPV PMPDLKNVKS KIGSTENLKH QPGGGKVQIV YKPVDLSKVT SKCGSLGNIH  240
HKPGGGQVEV KSEKLDFKDR VQSKIGSLDN ITHVPGGGNK KIETHKLTFR ENAKAKTDHG  300
AEIVYKSPVV SGDTSPRHLS NVSSTGSIDM VDSPQLATLA DEVSASLAKQ GL           352

SEQ ID NO: 7            moltype = DNA  length = 22
FEATURE                 Location/Qualifiers
source                  1..22
                        mol_type = other DNA
                        organism = synthetic construct
SEQUENCE: 7
ctaatacgac tcactatagg gc                                           22

SEQ ID NO: 8            moltype = DNA  length = 26
FEATURE                 Location/Qualifiers
source                  1..26
                        mol_type = other DNA
                        organism = synthetic construct
SEQUENCE: 8
ctcaatttc ttgtccacct tggtgc                                        26

SEQ ID NO: 9            moltype = DNA  length = 26
FEATURE                 Location/Qualifiers
source                  1..26
                        mol_type = other DNA
                        organism = synthetic construct
SEQUENCE: 9
ctcaagtttt ttgtccaccg tggtgc                                       26

SEQ ID NO: 10           moltype = AA  length = 225
FEATURE                 Location/Qualifiers
source                  1..225
                        mol_type = protein
                        organism = synthetic construct
SEQUENCE: 10
MDWVWNLLFL MAAAQSIQAQ IQLVQSGPEL KKPGETVKIS CKASGYPFTY HGMDWVKQAP  60
WGGLEWMGWI NTYSGVPTYA DDFKGRFAFS LETSVGTAYL QINNLKNEDT ATYFCARRRD  120
FTMDFWGQGT SVTVSSAKTT PPSVYPLAPG SAAQTNSMVT LGCLVKGYFP EPVTVTWNSG  180
SLSSGVHTFP AVLQSDLYTL SSSVTVPSST WPSETVTCNV AHPAS                  225

SEQ ID NO: 11           moltype = AA  length = 5
FEATURE                 Location/Qualifiers
source                  1..5
                        mol_type = protein
                        organism = synthetic construct
SEQUENCE: 11
YHGMD                                                              5

SEQ ID NO: 12           moltype = AA  length = 17
```

```
FEATURE                Location/Qualifiers
source                 1..17
                       mol_type = protein
                       organism = synthetic construct
SEQUENCE: 12
WINTYSGVPT YADDFKG                                           17

SEQ ID NO: 13          moltype = AA  length = 8
FEATURE                Location/Qualifiers
source                 1..8
                       mol_type = protein
                       organism = synthetic construct
SEQUENCE: 13
RRDFTMDF                                                     8

SEQ ID NO: 14          moltype = AA  length = 118
FEATURE                Location/Qualifiers
source                 1..118
                       mol_type = protein
                       organism = synthetic construct
SEQUENCE: 14
QVQLVQSGSE LKRPGASVKV SCKASGYSFT SYAVNWVRQA PGQGLEWVGW INTNTGNPTY  60
AQGFTGRFVF SLDTSVSTAY LQISSLKAAD TAVYYCARAR GQNGMDVWGQ GTTVTVSS    118

SEQ ID NO: 15          moltype = AA  length = 117
FEATURE                Location/Qualifiers
source                 1..117
                       mol_type = protein
                       organism = synthetic construct
SEQUENCE: 15
QVQLVQSGSE LKKPGASVKV SCKASGYTFT YHGMDWVRQA PGQGLEWMGW INTYSGVPTY  60
ADDFKGRFVF SLDTSVSTAY LQISSLKAED TAVYFCARRR DFTMDFWGQG TTVTVSS     117

SEQ ID NO: 16          moltype = AA  length = 230
FEATURE                Location/Qualifiers
source                 1..230
                       mol_type = protein
                       organism = synthetic construct
SEQUENCE: 16
MDSQAQVLIL LLLWVSGTCG NIVLSQSPSS LAVSPGEKVT MSCKSSQSLL NSRTRKNYLA  60
WFQQKPGQSP KLLIYWASTR ESGVPDRFTG SGSGTDFTLT ISSVQAEDLA VYYCKQSYTL  120
RTFGGGTNLE IKRADAAPTV SIFPPSSEQL TSGGASVVCF LNNFYPKDIN VKWKIDGSER  180
QNGVLNSWTD QDSKDSTYSM SSTLTLTKDE YERHNSYTCE ATHKTSTSPI            230

SEQ ID NO: 17          moltype = AA  length = 17
FEATURE                Location/Qualifiers
source                 1..17
                       mol_type = protein
                       organism = synthetic construct
SEQUENCE: 17
KSSQSLLNSR TRKNYLA                                           17

SEQ ID NO: 18          moltype = AA  length = 7
FEATURE                Location/Qualifiers
source                 1..7
                       mol_type = protein
                       organism = synthetic construct
SEQUENCE: 18
WASTRES                                                      7

SEQ ID NO: 19          moltype = AA  length = 8
FEATURE                Location/Qualifiers
source                 1..8
                       mol_type = protein
                       organism = synthetic construct
SEQUENCE: 19
KQSYTLRT                                                     8

SEQ ID NO: 20          moltype = AA  length = 114
FEATURE                Location/Qualifiers
source                 1..114
                       mol_type = protein
                       organism = synthetic construct
SEQUENCE: 20
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PQTFGGGTKV EIKR       114

SEQ ID NO: 21          moltype = AA  length = 113
FEATURE                Location/Qualifiers
```

```
source                  1..113
                        mol_type = protein
                        organism = synthetic construct
SEQUENCE: 21
NIVLTQSPDS LAVSLGERAT INCKSSQSLL NSRTRKNYLA WFQQKPGQPP KLLIYWASTR  60
ESGVPDRFSG SGSGTDFTLT ISSLQAEDVA VYYCKQSYTL RTFGGGTKVE IKR         113

SEQ ID NO: 22           moltype = AA  length = 113
FEATURE                 Location/Qualifiers
source                  1..113
                        mol_type = protein
                        organism = synthetic construct
SEQUENCE: 22
NIVLTQSPDS LAVSLGERAT INCKSSQSLL NSRTRKNYLA WFQQKPGQSP KLLIYWASTR  60
ESGVPDRFSG SGSGTDFTLT ISSLQAEDVA VYYCKQSYTL RTFGGGTKVE IKR         113

SEQ ID NO: 23           moltype = AA  length = 113
FEATURE                 Location/Qualifiers
source                  1..113
                        mol_type = protein
                        organism = synthetic construct
SEQUENCE: 23
DIVLTQSPDS LAVSLGERAT INCKSSQSLL NSRTRKNYLA WFQQKPGQSP KLLIYWASTR  60
ESGVPDRFSG SGSGTDFTLT ISSLQAEDVA VYYCKQSYTL RTFGGGTKVE IKR         113

SEQ ID NO: 24           moltype = AA  length = 10
FEATURE                 Location/Qualifiers
source                  1..10
                        mol_type = protein
                        organism = synthetic construct
SEQUENCE: 24
GYPFTYHGMD                                                         10

SEQ ID NO: 25           moltype = DNA  length = 351
FEATURE                 Location/Qualifiers
source                  1..351
                        mol_type = other DNA
                        organism = synthetic construct
SEQUENCE: 25
caggtccagt tggtgcagtc tggatctgag ctgaagaagc ctggagcctc cgtcaaggtg  60
tcctgcaagg cttctgggta tcccttcaca taccatggaa tggactgggt gcgtcaggct  120
cctggtcagg gtttagagtg gatgggctgg ataaacacct actctggagt gccaacatat  180
gctgatgact tcaagggacg atttgtgttc tctttggaca cctctgtctc tactgcctat  240
ttgcagatct cttctctcaa agccgaggac acggccgtgt atttttgtgc aagacggcgt  300
gattttacaa tggacttctg gggtcaagga accaccgtga ccgtctcctc a           351

SEQ ID NO: 26           moltype = DNA  length = 339
FEATURE                 Location/Qualifiers
source                  1..339
                        mol_type = other DNA
                        organism = synthetic construct
SEQUENCE: 26
aacatcgtgc tgacccagag ccccgatagc ctggccgtga gcctgggcga gagagccacc  60
atcaactgca agagcagcca gagcctgctg aacagcagga ccaggaagaa ctacctggcc  120
tggttccagc agaagcccgg ccagcccccc aagctgctga tctactgggc cagcaccagg  180
gagagcggcg tgcccgatag gttcagcggc agcggcagcg gcaccgattt caccctgacc  240
atcagcagcc tgcaggccga ggatgtggcc gtgtactact gcaagcagag ctacaccctg  300
agaaccttcg gcggcggcac caaggtggaa attaaacgt                         339

SEQ ID NO: 27           moltype = DNA  length = 339
FEATURE                 Location/Qualifiers
source                  1..339
                        mol_type = other DNA
                        organism = synthetic construct
SEQUENCE: 27
aacatcgtgc tgacccagag ccccgatagc ctggccgtga gcctgggcga gagagccacc  60
atcaactgca agagcagcca gagcctgctg aacagcagga ccaggaagaa ctacctggcc  120
tggttccagc agaagcccgg ccagagcccc aagctgctga tctactgggc cagcaccagg  180
gagagcggcg tgcccgatag gttcagcggc agcggcagcg gcaccgattt caccctgacc  240
atcagcagcc tgcaggccga ggatgtggcc gtgtactact gcaagcagag ctacaccctg  300
agaaccttcg gcggcggcac caaggtggaa attaaacgt                         339

SEQ ID NO: 28           moltype = DNA  length = 339
FEATURE                 Location/Qualifiers
source                  1..339
                        mol_type = other DNA
                        organism = synthetic construct
SEQUENCE: 28
gacatcgtgc tgacccagag ccccgatagc ctggccgtga gcctgggcga gagagccacc  60
```

```
atcaactgca agagcagcca gagcctgctg aacagcagga ccaggaagaa ctacctggcc  120
tggttccagc agaagcccgg ccagagcccc aagctgctga tctactgggc cagcaccagg  180
gagagcggcg tgcccgatag gttcagcggc agcggcagcg gcaccgattt caccctgacc  240
atcagcagcc tgcaggccga ggatgtggcc gtgtactact gcaagcagag ctacaccctg  300
agaaccttcg gcggcggcac caaggtggaa attaaacgt                         339

SEQ ID NO: 29          moltype = AA  length = 330
FEATURE                Location/Qualifiers
source                 1..330
                       mol_type = protein
                       organism = synthetic construct
SEQUENCE: 29
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNV KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 30          moltype = DNA  length = 990
FEATURE                Location/Qualifiers
source                 1..990
                       mol_type = other DNA
                       organism = synthetic construct
SEQUENCE: 30
gctagcacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                    990

SEQ ID NO: 31          moltype = DNA  length = 1343
FEATURE                Location/Qualifiers
source                 1..1343
                       mol_type = other DNA
                       organism = synthetic construct
SEQUENCE: 31
ggtgagtgga tccgcggccg ctaaactctg agggggtcgg atgacgtggc cattctttgc  60
ctaaagcatt gagtttactg caaggtcaga aaagcatgca aagccctcag aatggctgca  120
aagagctcca acaaaacaat ttagaacttt attaaggaat agggggaagc taggaagaaa  180
ctcaaaacat caagatttta aatacgcttc ttggtctcct tgctataatt atctgggata  240
agcatgctgt tttctgtctg tccctaacat gccctgtgat tatccgcaaa caacacaccc  300
aagggcagaa ctttgttact taaacaccat cctgtttgct tctttcctca gcctccacca  360
agggcccatc ggtcttcccc ctggcaccct cctccaagag cacctctggg ggcacagcgg  420
ccctgggctg cctggtcaag gactacttcc ccgaaccggt gacggtgtcg tggaactcag  480
gcgccctgac cagcggcgtg cacaccttcc cggctgtcct acagtcctca ggactctact  540
ccctcagcag cgtggtgacc gtgccctcca gcagcttggg cacccagacc tacatctgca  600
acgtgaatca caagcccagc aacaccaagg tggacaagag agttgagccc aaatcttgtg  660
acaaaactca cacatgccca ccgtgcccag cacctgaact cctgggggga ccgtcagtct  720
tcctcttccc cccaaaaccc aaggacaccc tcatgatctc ccggacccct gaggtcacat  780
gcgtggtggt ggacgtgagc cacgaagacc ctgaggtcaa gttcaactgg tacgtggacg  840
gcgtggaggt gcataatgcc aagacaaagc cgcgggagga gcagtacaac agcacgtacc  900
gtgtggtcag cgtcctcacc gtcctgcacc aggactggct gaatggcaag gagtacaagt  960
gcaaggtctc caacaaagcc ctcccagccc ccatcgagaa aaccatctcc aaagccaaag  1020
ggcagccccg agaaccacag gtgtacacgc tgcccccatc ccgggaggag atgaccaaga  1080
accaggtcag cctgacctgc ctggtcaaag gcttctatcc cagcgacatc gccgtggagt  1140
gggagagcaa tgggcagccg gagaacaact acaagaccac gcctcccgtg ctggactccg  1200
acggctcctt cttcctctat agcaagctca ccgtggacaa gagcaggtgg cagcagggga  1260
acgtcttctc atgctccgtg atgcatgagg ctctgcacaa ccactacacg cagaagagcc  1320
tctccctgtc cccgggtaaa tga                                           1343

SEQ ID NO: 32          moltype = AA  length = 106
FEATURE                Location/Qualifiers
source                 1..106
                       mol_type = protein
                       organism = synthetic construct
SEQUENCE: 32
```

-continued

```
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 33          moltype = DNA  length = 318
FEATURE                Location/Qualifiers
source                 1..318
                       mol_type = other DNA
                       organism = synthetic construct
SEQUENCE: 33
acggtggctg caccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 34          moltype = DNA  length = 671
FEATURE                Location/Qualifiers
source                 1..671
                       mol_type = other DNA
                       organism = synthetic construct
SEQUENCE: 34
cgtgagtgga tccgcggccg ctaaactctg agggggtcgg atgacgtggc cattctttgc  60
ctaaagcatt gagtttactg caaggtcaga aaagcatgca aagccctcag aatggctgca  120
aagagctcca acaaaacaat ttagaacttt attaaggaat agggggaagc taggaagaaa  180
ctcaaaacat caagatttta aatacgcttc ttggtctcct tgctataatt atctgggata  240
agcatgctgt tttctgtctg tccctaacat gccctgtgat tatccgcaaa caacacaccc  300
aagggcagaa ctttgttact taaacaccat cctgtttgct tctttcctca ggaactgtgg  360
ctgcaccatc tgtcttcatc ttcccgccat ctgatgagca gttgaaatct ggaactgcct  420
ctgttgtgtg cctgctgaat aacttctatc ccagagaggc caaagtacag tggaaggtgg  480
ataacgccct ccaatcgggt aactcccagg agagtgtcac agagcaggac agcaaggaca  540
gcacctacag cctcagcagc accctgacgc tgagcaaagc agactacgag aaacacaaag  600
tctacgcctg cgaagtcacc catcagggcc tgagctcgcc cgtcacaaag agcttcaaca  660
ggggagagtg t                                                       671
```